(12) United States Patent
Ostrand-Rosenberg

(10) Patent No.: US 10,377,810 B2
(45) Date of Patent: Aug. 13, 2019

(54) SOLUBLE CD80 AS A THERAPEUTIC TO REVERSE IMMUNE SUPPRESSION IN CANCER PATIENTS

(71) Applicant: UNIVERSITY OF MARYLAND, BALTIMORE COUNTY, Baltimore, MD (US)

(72) Inventor: Suzanne Ostrand-Rosenberg, Columbia, MD (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 65 days.

(21) Appl. No.: 15/492,535

(22) Filed: Apr. 20, 2017

(65) Prior Publication Data
US 2017/0226181 A1  Aug. 10, 2017

Related U.S. Application Data

(62) Division of application No. 14/617,090, filed on Feb. 9, 2015, now Pat. No. 9,650,429, which is a division of application No. 13/660,037, filed on Oct. 25, 2012, now Pat. No. 8,956,619.

(60) Provisional application No. 61/551,113, filed on Oct. 25, 2011.

(51) Int. Cl.
| | | |
|---|---|---|
| *C07K 14/00* | (2006.01) |
| *C07K 14/705* | (2006.01) |
| *A61K 39/395* | (2006.01) |
| *A61K 31/7088* | (2006.01) |
| *C07K 16/00* | (2006.01) |
| *C07K 16/28* | (2006.01) |

(52) U.S. Cl.
CPC .... *C07K 14/70532* (2013.01); *A61K 31/7088* (2013.01); *A61K 39/395* (2013.01); *C07K 14/00* (2013.01); *C07K 16/00* (2013.01); *C07K 16/2827* (2013.01); *C07K 2317/76* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 2010/0028341 A1 | 2/2010 | Hermans et al. |
| 2012/0039906 A1 | 2/2012 | Olive |
| 2014/0348832 A1* | 11/2014 | Zhu .............. C07K 14/70539 424/136.1 |

OTHER PUBLICATIONS

Fargeas et al (J. Exp. Med 182:667-675, 1995 (Year: 1995).*
Ascierto, P. A. et al. Clinical experiences with anti-CD137 and anti-PD1 therapeutic antibodies. Semin Oncol (2010) 37:508-516.
Azuma, T., S. et al. B7-H1 is a ubiquitous antiapoptotic receptor on cancer cells. *Blood* (2008.) 111:3635-3643.
Blank, C., I. et al. PD-L1/B7H-1 inhibits the effector phase of tumor rejection by T cell receptor (TCR) transgenic CD8+ T cells. *Cancer Res* (2004) 64:1140-1145.
Bosch, J. J., et al. MHC class II-transduced tumor cells originating in the immune-privileged eye prime and boost CD4(+) T lymphocytes that cross-react with primary and metastatic uveal melanoma cells. Cancer Res (2007) 67:4499-4506.
Brahmer, J. R., et al. Phase I study of single-agent anti-programmed death-1 (MDX-1106) in refractory solid tumors: safety, clinical activity, pharmacodynamics, and immunologic correlates. *J Clin Oncol* (2010) 28:3167-3175.
Brahmer, J. R. et al. Safety and activity of anti-PD-L1 antibody in patients with advanced cancer. *N Engl J Med* (2012) 366:2455-2465.
Brown, J. A. et al. Blockade of programmed death-1 ligands on dendritic cells enhances T cell activation and cytokine production. *J Immunol* (2003) 170:1257-1266.
Butte, M. J. et al. Programmed death-1 ligand 1 interacts specifically with the B7-1 costimulatory molecule to inhibit T cell responses. Immunity (2007) 27:111-122.
Butte, M. J. et al. Interaction of human PD-L1 and B7-1. *Mol Immunol* (2008) 45:3567-3572.
Chen, L. Co-inhibitory molecules of the B7-CD28 family in the control off T-cell immunity. *Nat Rev Immunol* (2004) 4:336-347.
Curiel, T. J. et al. Blockade of B7-H1 improves myeloid dendritic cell-mediated antitumor immunity. *Nature Medicine* (2003) 9:562-567.
Dissanayake, S. K. et al. Activation of tumor-specific CD4(+) T lymphocytes by major histocompatibility complex class II tumor cell vaccines: a novel cell-based immunotherapy. *Cancer Res* (2004) 64:1867-1874.
Dong, H. et al. Tumor-associated B7-H1 promotes T-cell apoptosis: a potential mechanism of immune evasion. *Nat Med* (2002) 8:793-800.
Francisco, L. M. et al. PD-L1 regulates the development, maintenance, and function of induced regulatory T cells. *The Journal of Experimental Medicine* (2009) 206:3015-3029.
Haile, S. T. et al. Tumor cell programmed death ligand 1-mediated T cell suppression is overcome by coexpression of CD80. J Immunol (2011) 186:6822-6829.
He, Wei et al. "In vitro co-stimulation of anti-tumor activity by soluble B7 molecules." Acta Biochimica Polonica, vol. 55, No. Apr. 2006, pp. 807-813.
Hirano, F., K. Blockade of B7-H1 and PD-1 by monoclonal antibodies potentiates cancer therapeutic immunity. *Cancer Res* (2005) 65:1089-1096.
Jenkins, M., P. et al. CD28 delivers a costimulatory signal involved in antigen-specific IL-2 production by human T cells. *J Immunol* (1991)147:2461-2467.

(Continued)

Primary Examiner — Lei Yao
(74) Attorney, Agent, or Firm — Tristan A. Fuierer; Marianne Fuierer; Olive Law Group, PLLC

(57) ABSTRACT

The present invention provides for a therapeutic cancer treatment using a soluble CD80 fusion protein that binds to PDL1 and inhibits PDL1-PD1 interactions thereby overcoming PDL1-induced immune suppression and restoring T cell activation.

4 Claims, 11 Drawing Sheets
Specification includes a Sequence Listing.

(56) References Cited

OTHER PUBLICATIONS

Kakoulidou, M. et al. "Human Soluble CD80 is Generated by Alternative Splicing, and Recombinant Soluble CD80 Binds to CD28 and CD152 Influencing T-cell Activation." Scandinavian Journal of Immunology, 2007, 66, pp. 529-537.
Latchman, Y. E. et al. PD-L1-deficient mice show that PD-L1 on T cells, antigen-presenting cells, and host tissues negatively regulates T cells. *Proc Natl Acad Sci USA* (2004) 101:10691-10696.
Liu, Aihong et al. "Combination B7-FC Fusion Protein Treatment and Treg Cell Depletion Therapy." *Clin Cancer Res*, 11(23), Dec. 1, 2005, pp. 8492-8502.
Mu, C. Y. et al. Highexpression of PD-L1 in lung cancer may contribute to poor prognosis and tumor cells immune escape through suppressing tumor infiltrating dendritic cells maturation. *Medical Oncology* (2011) 28:682-688.
Norton, S., L. et al. The CD28 ligand, B7, enhances IL-2 production by providing a costimulatory signal to T cells. *J Immunol* (1992) 149:1556-1617.
Park, J. J. et al. B7-H1/CD80 interaction is required for the induction and maintenance of peripheral T-cell tolerance. Blood (2010) 116:1291-1298.
Parsa, A. T. et al. Loss of tumor suppressor PTEN function increases B7-H1 expression and immunoresistance in glioma. *Nature Medicine* (2007) 13:84-88.
Peach, R. J. et al. Both extracellular immunoglobin-like domains of CD80 contain residues critical for binding T cell surface receptors CTLA-4 and CD28. *The Journal of biological chemistry* ((1995) 270:21181-21187.
Peng, W. et al. PD-1 Blockade Enhances T Cell Migration to Tumors by Elevating IFN-gamma Inducible Chemokines. *Cancer Res.* (2012) (soon to be published).
Pulaski, B. A. et al. Reduction of established spontaneous mammary carcinoma metastases following immunotherapy with major histocompatibility complex class II and B7.1 cell-based tumor vaccines. *Cancer Res* (1998) 58:1486-1493.
Sakthivel, P. et al. Therapeutic intervention in cancer and chronic viral infections: Antibody mediated manipulation of PD-1/PD-L1 interaction. Rev Recent Clin Trials. (2011) 7:10-23.
Salomon, B. et al. Complexities of CD28/B7: CTLA-4 costimulatory pathways in autoimmunity and transplantation. *Annual review of immunology* ((2001) 19:225-252.
Schmidt, S. R. Fusion-proteins as biopharmaceuticals—applications and challenges. Curr Opin Drug Discov Devel (2009) 12:284-295.
Srivastava, M. K. et al. Lung cancer patients' CD4(+) T cells are activated in vitro by MHC II cell-based vaccines despite the presence of myeloid-derived suppressor cells.
*Cancer Immunol Immunother* (2008) 57:1493-1504.
Srivastava, M. K. et al. MHC II lung cancer vaccines prime and boost tumor-specific CD4+ Tcells that cross-react with multiple histologic subtypes of nonsmall cell lung cancer cells. *Int J Cancer* (2010) 127:2612-2621.
Stamper, C. C. et al. Crystal structure of the B7-1/CTLA-4 complex that inhibits human immune responses. *Nature* (2001) 410:608-611.
Strome, S. E. et al. B7-H1 blockade augments adoptive T-cell immunotherapy for squamous cell carcinoma. *Cancer Res* (2003) 63:6501-6505.
Thompson, R. H. et al. Tumor B7-H1 is associated with poor prognosis in renal cell carcinoma patients with long-term follow-up. *Cancer Res* (2006) 66:3381-3385.
Thompson, J. A. et al. The absence of invariant chain in MHC II cancer vaccines enhances the activation of tumor-reactive type 1 CD4+ T lymphocytes. *Cancer Immunol Immunother* (2008) 57:389-398.
Topalian, S. L. et al. Safety, activity, and immune correlates of anti-PD-1 antibody in cancer. *N Engl J Med* (2012) 366:2443-2454.
Zhang, L. et al. PD-1/PD-L1 interactions inhibit antitumor immune responses in a murine acute myeloid leukemia model. *Blood* (2009) 114:1545-1552.
CD80-Fc fusion, R&D system, product sheet, 2016.

* cited by examiner

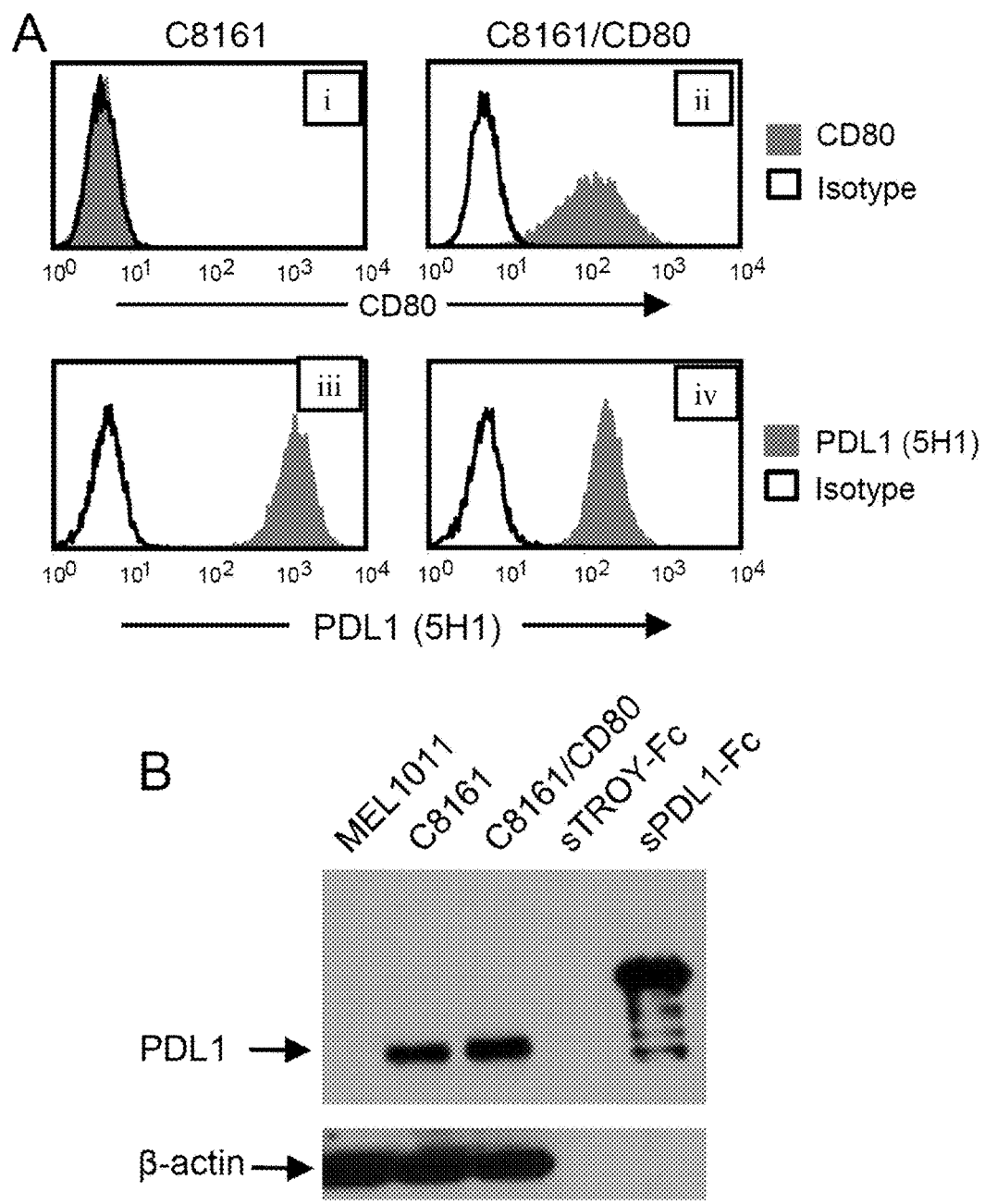
Figure 1 A and B

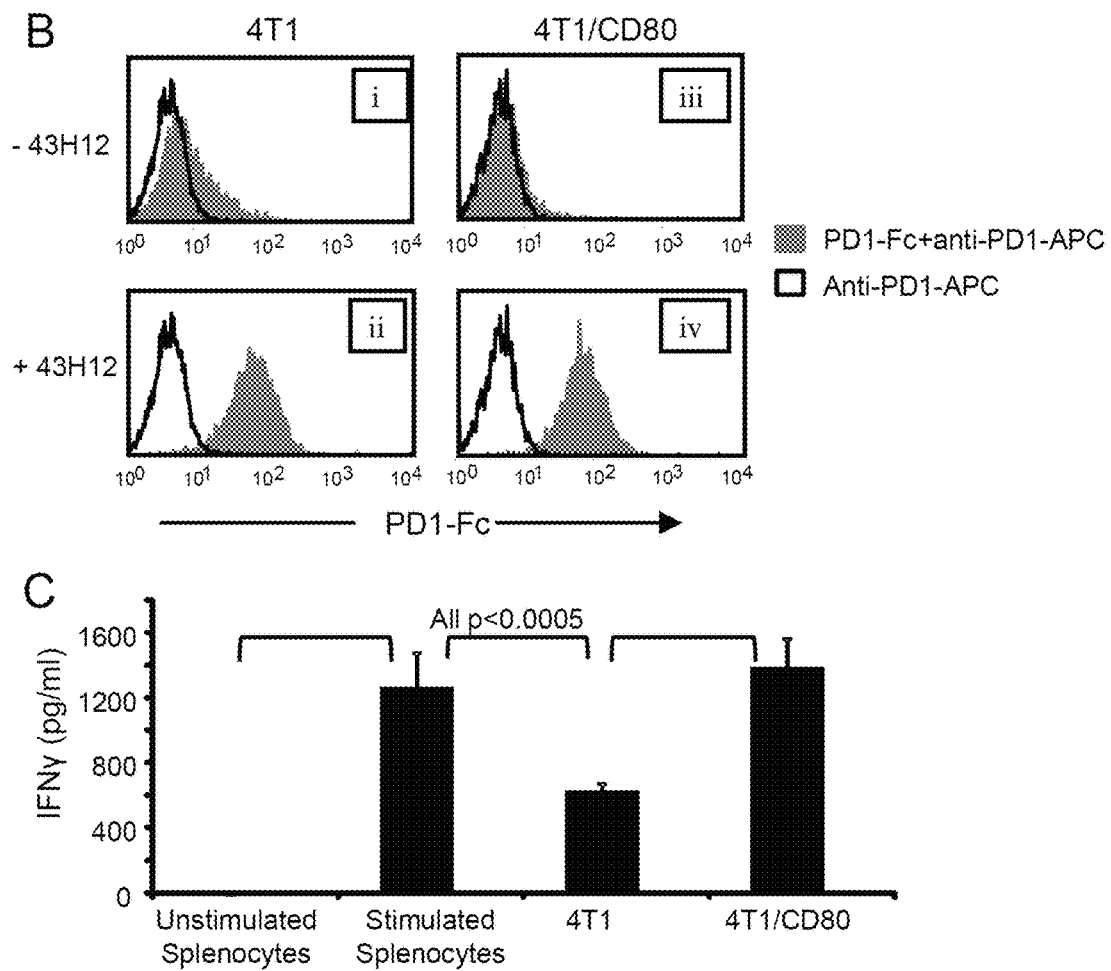
Figure 2 B and C

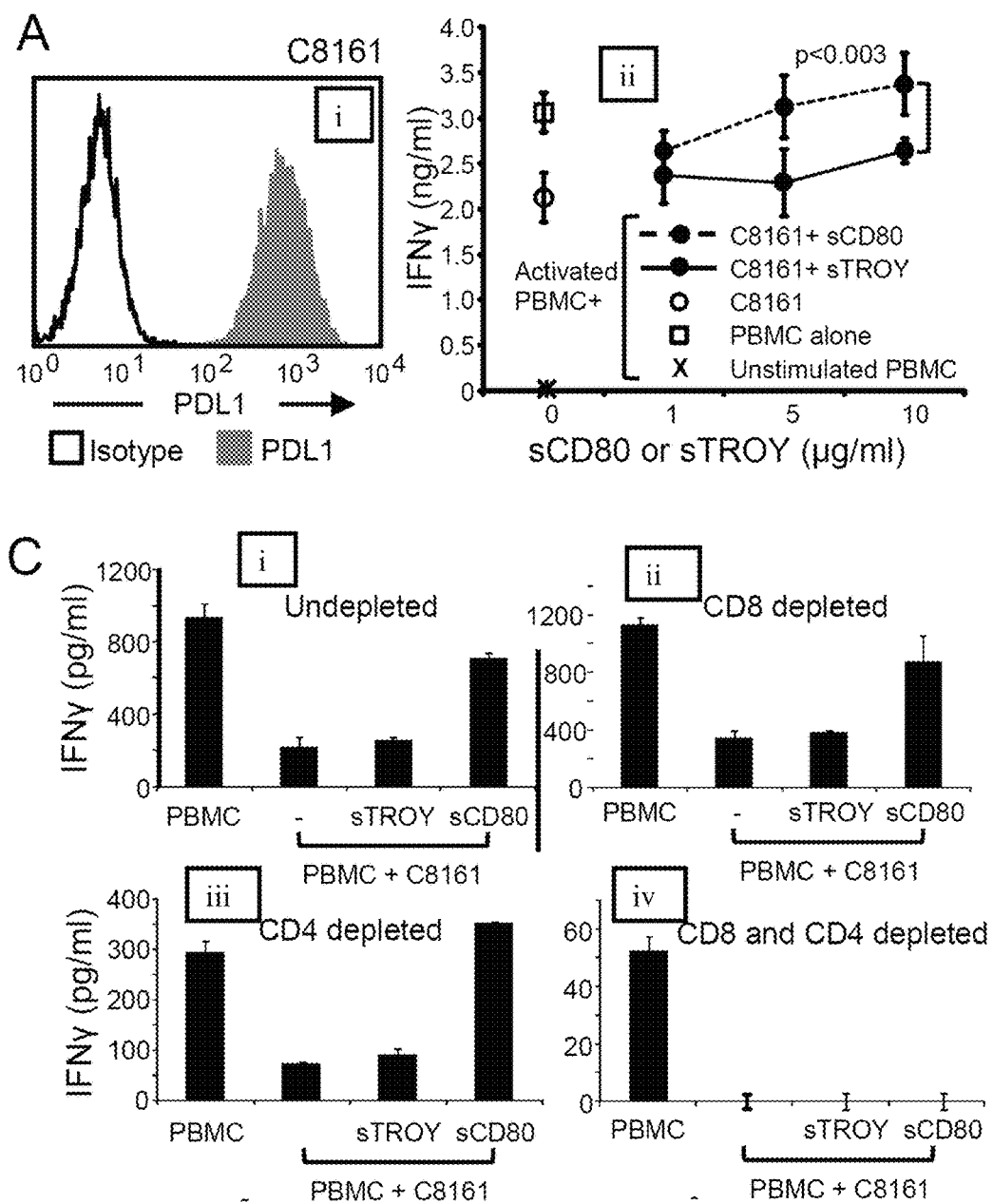
Figure 3 A and C

SEQUENCE LISTING

```
<160> NUMBER OF SEQ ID NOS: 16

<210> SEQ ID NO 1
<211> LENGTH: 762
<212> TYPE: DNA
<213> ORGANISM: Artificial Sequence
<220> FEATURE:
<223> OTHER INFORMATION: Synthetic Construct

<400> SEQUENCE: 1
ggccacacac ggaggcaggg aatatcacca tccaagtgtc catacctcaa tttctttcag      60
ctcttggtgc tggctggtct ttctcacttc tgttcaggtg ttatccacgt gaccaaggaa     120
gtgaaagaag tagcaacgct gtcctgtggt cacaatgttt ctgttgaaga gctggcacaa     180
actcgcatct actggcaaaa ggagaagaaa atggtgctga ctatgatgtc tggggacatg     240
gatatatggc ccgagtacaa gaaccggacc atctttgata tcactaataa cctctccatt     300
gtgatcctgg ctctgcgccc atctgacgag ggcacatacg agtgtgttgt tctgaagtat     360 gaaaagacg ctttcaagcg ggaacacctg gctgaagtga cgttatcagt caaagctgac     420
ttccctacac ctagtatatc tgactttgaa attccaactt ctaatattag aaggataatt     480
tgctcaacct ctggaggttt tccagagcct cacctctcct ggttggaaaa tggagaagaa     540
ttaaatgcca tcaacacaac agtttcccaa gatcctgaaa ctgagctcta tgctgttagc     600
agcaaactgg atttcaatat gacaaccaac cacagcttca tgtgtctcat caagtatgga     660
cattcaagag tgaatcagac cttcaactgg aatacaacca agcaagagca ttttcctgat     720
```
aacctgctcc atcctgggc cattaccta atctcagtaa at 762

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
gcgcggatcc ggccacacac ggagg 25

<210> SEQ ID NO 3
<211> LENGTH: 26
<212> TYPE: DNA
<213> ORGANISM: Artificial Sequence
<220> FEATURE:
<223> OTHER INFORMATION: Synthetic Construct

<400> SEQUENCE: 3
gagttttgtc atttactgag attaag 26

<210> SEQ ID NO 4
<211> LENGTH: 254
<212> TYPE: PRT
<213> ORGANISM: Artificial Sequence
<220> FEATURE:
<223> OTHER INFORMATION: Synthetic Construct

<400> SEQUENCE: 4

```
Gly His Thr Arg Arg Gln Gly Thr Ser Pro Ser Lys Cys Pro Tyr Leu
1               5                   10                  15

Asn Phe Phe Gln Leu Leu Val Leu Ala Gly Leu Ser His Phe Cys Ser
            20                  25                  30

Gly Val Ile His Val Thr Lys Glu Val Lys Glu Val Ala Thr Leu Ser
        35                  40                  45

Cys Gly His Asn Val Ser Val Glu Glu Leu Ala Gln Thr Arg Ile Tyr
    50                  55                  60

Trp Gln Lys Glu Lys Lys Met Val Leu Thr Met Met Ser Gly Asp Met
65                  70                  75                  80

Asn Ile Trp Pro Glu Tyr Lys Asn Arg Thr Ile Phe Asp Ile Thr Asn
                85                  90                  95

Asn Leu Ser Ile Val Ile Leu Ala Leu Arg Pro Ser Asp Glu Gly Thr
            100                 105                 110

Tyr Glu Cys Val Val Leu Lys Tyr Glu Lys Asp Ala Phe Lys Arg Glu
        115                 120                 125

His Leu Ala Glu Val Thr Leu Ser Val Lys Ala Asp Phe Pro Thr Pro
    130                 135                 140

Ser Ile Ser Asp Phe Glu Ile Pro Thr Ser Asn Ile Arg Arg Ile Ile
145                 150                 155                 160

Cys Ser Thr Ser Gly Gly Phe Pro Glu Pro His Leu Ser Trp Leu Glu
                165                 170                 175

Asn Gly Glu Glu Leu Asn Ala Ile Asn Thr Thr Val Ser Gln Asp Pro
            180                 185                 190

Glu Thr Glu Leu Tyr Ala Val Ser Ser Lys Leu Asp Phe Asn Met Thr
        195                 200                 205

Thr Asn His Ser Phe Met Cys Leu Ile Lys Tyr Gly His Leu Arg Val
    210                 215                 220

Asn Gln Thr Phe Asn Trp Asn Thr Thr Lys Gln Glu His Phe Pro Asp
```

Asn Leu Leu Pro Ser Trp Ala Ile Thr Leu Ile Ser Val Asn
              245                 250

<210> SEQ ID NO 5
<211> LENGTH: 681
<212> TYPE: DNA
<213> ORGANISM: Artificial Sequence
<220> FEATURE:
<223> OTHER INFORMATION: Synthetic Construct

<400> SEQUENCE: 5

```
gacaaaactc acacatgccc accgtgccca gcacctgaac tcctgggggg accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc cccatcgaga aaaccatctc caaagccaaa   360
gggcagcccc gagaaccaca ggtgtacacc ctgcccccat cccgggatga gctgaccaag   420
aaccaggtca gcctgacctg cctggtcaaa ggcttctatc ccagcgacat cgccgtggag   480
tgggagagca atgggcagcc ggagaacaac tacaagacca cgcctcccgt gctggactcc   540
gacggctcct tcttcctcta cagcaagctc accgtggaca agagcaggtg gcagcagggg   600
aacgtcttct catgctccgt gatgcacgag gctctgcaca accactacac gcagaagagc   660
ctctccctgt ctccgggtaa a                                             681
```

<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6

```
ctcagtaaat gacaaaactc acaca                                          25
```

<210> SEQ ID NO 7
<211> LENGTH: 46
<212> TYPE: DNA
<213> ORGANISM: Artificial Sequence
<220> FEATURE:
<223> OTHER INFORMATION: Synthetic Construct

<400> SEQUENCE: 7

```
gcgcaagctt ttagtgatgg tgatggtgat gtttacccgg agacag               46
```

<210> SEQ ID NO 8
<211> LENGTH: 227
<212> TYPE: PRT
<213> ORGANISM: Artificial Sequence
<220> FEATURE:
<223> OTHER INFORMATION: Synthetic Construct

<400> SEQUENCE: 8

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30

```
Ile Ser Arg Thr Pro Gly Val Thr Cys Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
210                 215                 220
Pro Gly Lys
225

<210> SEQ ID NO 9
<211> LENGTH: 208
<212> TYPE: PRT
<213> ORGANISM: Artificial Sequence
<220> FEATURE:
<223> OTHER INFORMATION: Synthetic Construct

<400> SEQUENCE: 9

Val Ile His Val Thr Lys Glu Val Lys Glu Val Ala Thr Leu Ser Cys
 1               5                  10                  15
Gly His Asn Val Ser Val Glu Glu Leu Ala Gln Thr Arg Ile Tyr Trp
             20                  25                  30
Gln Lys Glu Lys Lys Met Val Leu Thr Met Met Ser Gly Asp Met Asn
         35                  40                  45
Ile Trp Pro Glu Tyr Lys Asn Arg Thr Ile Phe Asp Ile Thr Asn Asn
 50                  55                  60
Leu Ser Ile Val Ile Leu Ala Leu Arg Pro Ser Asp Glu Gly Thr Tyr
 65                  70                  75                  80
Glu Cys Val Val Leu Lys Tyr Glu Lys Asp Ala Phe Lys Arg Glu His
                 85                  90                  95
Leu Ala Glu Val Thr Leu Ser Val Lys Ala Asp Phe Pro Thr Pro Ser
            100                 105                 110
Ile Ser Asp Phe Glu Ile Pro Thr Ser Asn Ile Arg Arg Ile Ile Cys
        115                 120                 125
Ser Thr Ser Gly Gly Phe Pro Glu Pro His Leu Ser Trp Leu Glu Asn
130                 135                 140
Gly Glu Glu Leu Asn Ala Ile Asn Thr Thr Val Ser Gln Asp Pro Glu
145                 150                 155                 160
```

```
Thr Glu Leu Tyr Ala Val Ser Ser Lys Leu Asp Phe Asn Met Thr Thr
            165                 170                 175

Asn His Ser Phe Met Cys Leu Ile Lys Tyr Gly His Leu Arg Val Asn
        180                 185                 190

Gln Thr Phe Asn Trp Asn Thr Thr Lys Gln Glu His Phe Pro Asp Asn
    195                 200                 205
```

<210> SEQ ID NO 10
<211> LENGTH: 34
<212> TYPE: PRT
<213> ORGANISM: Artificial Sequence
<220> FEATURE:
<223> OTHER INFORMATION: Synthetic Construct

<400> SEQUENCE: 10

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly
```

<210> SEQ ID NO 11
<211> LENGTH: 46
<212> TYPE: PRT
<213> ORGANISM: Artificial Sequence
<220> FEATURE:
<223> OTHER INFORMATION: Synthetic Construct

<400> SEQUENCE: 11

```
Leu Leu Pro Ser Trp Ala Ile Thr Leu Ile Ser Val Asn Gly Ile Phe
1               5                   10                  15

Val Ile Cys Cys Leu Thr Tyr Cys Phe Ala Pro Arg Cys Arg Glu Arg
            20                  25                  30

Arg Arg Asn Glu Arg Leu Arg Arg Glu Ser Val Arg Pro Val
            35                  40                  45
```

<210> SEQ ID NO 12
<211> LENGTH: 232
<212> TYPE: PRT
<213> ORGANISM: Artificial Sequence
<220> FEATURE:
<223> OTHER INFORMATION: Synthetic Construct

<400> SEQUENCE: 12

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Gly Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125
```

```
Arg Glu Pro Gln Val Tyr Thr Leu Pro Pro Ser Arg Asp Glu Leu Thr
            130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230
```

<210> SEQ ID NO 13
<211> LENGTH: 696
<212> TYPE: DNA
<213> ORGANISM: Artificial Sequence
<220> FEATURE:
<223> OTHER INFORMATION: Synthetic Construct

<400> SEQUENCE: 13

```
gagcccaaat cttgtgacaa aactcacaca tgcccaccgt gcccagcacc tgaactcctg      60
gggggaccgt cagtcttcct cttccccca  aaacccaagg acaccctcat gatctcccgg     120
acccctgggg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga acaactacaa gaccacgcct     540
cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccg ggtaaa                                696
```

<210> SEQ ID NO 14
<211> LENGTH: 254
<212> TYPE: PRT
<213> ORGANISM: Artificial Sequence
<220> FEATURE:
<223> OTHER INFORMATION: Synthetic Construct

<400> SEQUENCE: 14

```
Val Ile His Val Thr Lys Glu Val Lys Glu Val Ala Thr Leu Ser Cys
1               5                   10                  15
Gly His Asn Val Ser Val Glu Glu Leu Ala Gln Thr Arg Ile Tyr Trp
            20                  25                  30
Gln Lys Glu Lys Lys Met Val Leu Thr Met Met Ser Gly Asp Met Asn
        35                  40                  45
Ile Trp Pro Glu Tyr Lys Asn Arg Thr Ile Phe Asp Ile Thr Asn Asn
    50                  55                  60
Leu Ser Ile Val Ile Leu Ala Leu Arg Pro Ser Asp Glu Gly Thr Tyr
```

```
                65                  70                  75                  80
Glu Cys Val Val Leu Lys Tyr Glu Lys Asp Ala Phe Lys Arg Glu Ala
                    85                  90                  95
Ala Ala Ala Val Thr Leu Ser Val Lys Ala Asp Phe Pro Thr Pro Ser
                100                 105                 110
Ile Ser Asp Phe Glu Ile Pro Thr Ser Asn Ile Arg Arg Ile Ile Cys
                115                 120                 125
Ser Thr Ser Gly Gly Phe Pro Glu Pro His Leu Ser Trp Leu Glu Asn
            130                 135                 140
Gly Glu Glu Leu Asn Ala Ile Asn Thr Thr Val Ser Gln Asp Pro Glu
145                 150                 155                 160
Thr Glu Leu Tyr Ala Val Ser Ser Lys Leu Asp Phe Asn Met Thr Thr
                165                 170                 175
Asn His Ser Phe Met Cys Leu Ile Lys Tyr Gly His Leu Arg Val Asn
            180                 185                 190
Gln Thr Phe Asn Trp Asn Thr Thr Lys Gln Glu His Phe Pro Asp Asn
                195                 200                 205
Leu Leu Pro Ser Trp Ala Ile Thr Leu Ile Ser Val Asn Gly Ile Phe
            210                 215                 220
Val Ile Cys Cys Leu Thr Tyr Cys Phe Ala Pro Arg Cys Arg Glu Arg
225                 230                 235                 240
Arg Arg Asn Glu Arg Leu Arg Arg Glu Ser Val Arg Pro Val
                245                 250

<210> SEQ ID NO 15
<211> LENGTH: 208
<212> TYPE: PRT
<213> ORGANISM: Artificial Sequence
<220> FEATURE:
<223> OTHER INFORMATION: Synthetic Construct

<400> SEQUENCE: 15

Val Ile His Val Thr Lys Glu Val Lys Glu Val Ala Thr Leu Ser Cys
1               5                   10                  15
Gly His Asn Val Ser Val Glu Glu Leu Ala Gln Thr Arg Ile Tyr Trp
                20                  25                  30
Gln Lys Glu Lys Lys Met Val Leu Thr Met Met Ser Gly Asp Met Asn
            35                  40                  45
Ile Trp Pro Glu Tyr Lys Asn Arg Thr Ile Phe Asp Ile Thr Asn Asn
        50                  55                  60
Leu Ser Ile Val Ile Leu Ala Leu Arg Pro Ser Asp Glu Gly Thr Tyr
65                  70                  75                  80
Glu Cys Val Val Leu Lys Tyr Glu Lys Asp Ala Phe Lys Arg Glu Ala
                85                  90                  95
Ala Ala Ala Val Thr Leu Ser Val Lys Ala Asp Phe Pro Thr Pro Ser
                100                 105                 110
Ile Ser Asp Phe Glu Ile Pro Thr Ser Asn Ile Arg Arg Ile Ile Cys
                115                 120                 125
Ser Thr Ser Gly Gly Phe Pro Glu Pro His Leu Ser Trp Leu Glu Asn
            130                 135                 140
Gly Glu Glu Leu Asn Ala Ile Asn Thr Thr Val Ser Gln Asp Pro Glu
145                 150                 155                 160
Thr Glu Leu Tyr Ala Val Ser Ser Lys Leu Asp Phe Asn Met Thr Thr
                165                 170                 175
Asn His Ser Phe Met Cys Leu Ile Lys Tyr Gly His Leu Arg Val Asn
```

```
                    180             185             190
Gln Thr Phe Asn Trp Asn Thr Thr Lys Gln Glu His Phe Pro Asp Asn
            195                 200             205

<210> SEQ ID NO 16
<211> LENGTH: 17
<212> TYPE: PRT
<213> ORGANISM: Artificial Sequence
<220> FEATURE:
<223> OTHER INFORMATION: Synthetic construct

<400> SEQUENCE: 16

Ile Ser Gln Ala Val His Ala Ala His Ala Glu Ile Asn Glu Ala Gly
1               5                   10                  15

Arg
```

SOLUBLE CD80 AS A THERAPEUTIC TO REVERSE IMMUNE SUPPRESSION IN CANCER PATIENTS

CROSS-REFERENCE TO RELATED APPLICATION

The present application is a divisional application that claims priority to U.S. patent application Ser. No. 14/617,090 filed on Feb. 9, 2015, now U.S. Pat. No. 9,650,429, which in turn claimed priority to U.S. patent application Ser. No. 13/660,037 filed on Oct. 25, 2012, now U.S. Pat. No. 8,956,619 which in turn claims priority to U.S. Provisional Patent Application No. 61/551,113 filed on Oct. 25, 2011, the contents of which are hereby incorporated by reference herein for all purposes.

STATEMENT OF GOVERNMENT RIGHTS

This work was supported by grants from the National Institute of Health under contract number RO1CA84232 and RO1CA115880 and the United States Government has rights to this invention.

BACKGROUND OF THE INVENTION

Field of the Invention

The present invention relates generally to the field of cancer treatment, and more particularly, to a soluble CD80 protein that interacts with programmed death ligand 1 (PD-L1) and thereby inhibiting the interaction of PD-L1 with T-cell expressed programmed death 1 (PD1) receptor, and thus, minimizing PD-L1 mediated immune suppression.

Description of the Related Art Technical Field

Tumor-induced immune suppression is a major obstacle for therapies aimed at activating an individual's immune system to eliminate autologous cancer cells. Various mechanisms contribute to this immune suppression. A major contributor is the co-inhibitory molecule Programmed Death Ligand-1 (PDL1), also known as B7 homolog 1 (B7-H1) or CD274. PDL1 obstructs anti-tumor immunity by (i) tolerizing tumor-reactive T cells by binding to its receptor PD1 (CD279) on T cells (1, 2); (ii) rendering tumor cells resistant to CD8+ T cell and FasL-mediated lysis by PD-1 signaling through tumor cell-expressed PDL1 (3); (iii) tolerizing T cells by reverse signaling through T cell-expressed CD80 (4, 5); and (iv) promoting the development and maintenance of induced T regulatory cells (6).

Most malignant cells constitutively express or are induced by IFNγ to express PDL1 (1, 3, 7, 8), and the loss of tumor suppressor genes can increase tumor cell expression of PDL1 (9). Expression of PDL1 by human cancer cells is a marker for poor prognosis (7, 10, 11). Therefore, PDL1 is a major obstacle to natural anti-tumor immunity and to cancer immunotherapies requiring activation of host T cell-mediated anti-tumor immunity. This concept is supported by studies demonstrating that antibody blocking of PDL1-PD1 interactions improves T cell activation and reduces tumor progression, and that antibody blocking of PDL1 reverse signaling through T cell-expressed CD80 prevents T cell anergy (5). The critical role of PDL1 has recently been further supported by phase I/II clinical trials in which mAb to PDL1 or PD1 have delayed tumor progression in some patients with cutaneous melanoma, renal cell carcinoma, non-small cell lung cancer, and hormone refractory prostate cancer (16-20). Although antibodies to PDL1 or PD1 have shown therapeutic efficacy in a subset of cancer patients, the majority of patients do not benefit from antibody treatment.

Thus, there is needed a novel mechanism for regulating PD-L1 function that will lead to a new universally applicable treatment for minimizing PD-L1-mediated immune suppression in cancer patients and that is more effective than currently available mAbs to PD-1 or PD-L1.

SUMMARY OF THE INVENTION

The present invention relates to the discovery that the use of a soluble CD80 molecule blocks PD-L1 function and enables the boosting of primed tumor-reactive T cells despite the presence of PD-L1 thereby identifying a new and novel mechanism for regulating this immunosuppressive molecule.

In one aspect, the present invention provides for a binding complex to activate tumor-specific T cells, wherein the binding complex comprising a soluble chimeric polypeptide and PDL1, wherein the soluble chimeric polypeptide comprises a CD80 amino acid sequence, a modified sequence having at least 95% homology or a fragment thereof fused to Fc IgG1.

In another aspect the present invention provides for a method to inhibit and/or reduce binding of PDL1 to PD1 thereby increasing immune response against tumor cells, the method comprising:
a. providing a chimeric polypeptide comprising CD80 amino acid sequence, a modified sequence having at least 95% homology or a fragment thereof fused to Fc of IgG1; and
b. contacting a tumor cell with the chimeric polypeptide wherein the chimeric polypeptide binds with PDL1 of the tumor cell.

In yet another aspect the present invention provides for a method of blocking of PDL1-PD1 interactions thereby improving T cell activation and reducing tumor progression, the method comprising:
a. providing a soluble chimeric protein comprising at least two extracellular domains of CD80 fused to Fc of IgG1; and
b. contacting a tumor cell with the soluble chimeric protein wherein the CD80 protein binds with PDL1 of the tumor cell.

In a further aspect the present invention provides for polynucleotide sequences having a nucleic acid sequence encoding the soluble chimeric polypeptide of the present invention. The polynucleotides can be included in an expression vector useful for expressing chimeric polypeptides and can be used as a DNA vaccine that induces an immunomodulating effect thereby inhibiting the binding of PDL1 to PD1 and reducing immune suppression effected by a tumor cell.

In another aspect, the present invention provides for a method for reversing PD-L1 mediated immune suppression in a subject wherein the method comprises administering a therapeutically effective amount of a soluble fusion protein consisting of the extracellular domains of CD80 fused to an Fc domain of IgG1, or a polynucleotide encoding same thereby inhibiting, reversing or reducing PD-L1 mediated immune suppression.

In a further aspect, the present invention provides for a method for identifying agents that modulate binding or interaction between PD-L1 and PD1. In one embodiment, a method includes contacting a soluble polypeptide having at least of the extracellular domains of CD80 under conditions allowing the soluble polypeptide and the PD-L1 to bind, in the presence and absence of a test agent, and detecting binding of the soluble polypeptide to PD-L1 in the presence and absence of the test agent. Decreased binding of the soluble polypeptide to PD-L1 in the presence of the test agent identifies a test agent that inhibits or reduces binding between PD-L1 and PD1.

In another embodiment, the present invention contemplates an isolated and purified chimeric peptide that comprises the amino acid residue sequences of SEQ ID NOs: 4 and 8 or sequences having at least 95% homology thereto.

In yet another embodiment, the chimeric polypeptide comprises or consists of SEQ ID NO: 9 (extracellur domain of CD80) with or without the signaling residues as defined in SEQ ID NO: 10 and/or the transmembrane residues as defined in SEQ ID NO: 11. The CD80 amino acid residues correspond to P33681 (CD80 HUMAN) as found on UniportkB. The FcIgG1 sequence of SEQ ID NO: 12, encoded by SEQ ID NO: 13 is fused to the CD80 sequence.

In addition to the sequences of the two extracellular domains of the CD 80 peptide, as defined in SEQ ID NO: 9, additional peptide sequence modification may be included, such as minor variations, deletions, substitutions or derivitizations of the amino acid sequence of the sequences disclosed herein, so long as the peptide has substantially the same activity or function as the unmodified peptides. A modified peptide will retain activity or function associated with the unmodified peptide, the modified peptide will generally have an amino acid sequence "substantially homologous" with the amino acid sequence of the unmodified sequence.

The present invention provides for a soluble CD80 molecule comprising at least the two extracellular domains of CD80 and has been found to be more effective than anti-PD-L1 or PD-1 mAbs in reversing PD-L1 mediated immune suppression thereby providing for a novel and effective cancer immunotherapy.

Yet another aspect of the present invention relates to a method of making a CD80 linear chimera comprising the steps of covalently attaching amino acid residues of the Fc domain of IgG1 to at least a linear sequence of amino acid residues of CD80 that bind to the PDL1 protein thereby forming the chimera.

In a still further aspect, the present invention relates to a mutated CD80 sequence comprising or consisting of SEQ ID NO: 15, wherein residues 96, 97 and 99 have been substituted with an alanine residue thereby providing for a soluble CD80 sequence that does not bind to Cytotoxic T-Lymphocyte Antigen 4 (CTLA4). SEQ ID NO: 15 may be used alone or with the transmembrane sequence SEQ ID NO: 11 and/or signaling sequence SEQ ID NO: 10. This mutated CD80 peptide may be combined with FcIgG1 to provide another embodiment of the present invention to ensure that the chimera does not bind to CTLA4.

The CD80 linear epitope peptide/IgG1 protein chimera may be administered alone or in a pharmaceutical composition as a vaccine in a therapeutically effective amount to elicit an enhanced immune response or a protective immune response in an animal.

The chimera may further include a linker or amino acid spacer linking the CD80 linear epitope peptide and Fc IgG1 protein.

Other features and advantages of the invention will be apparent from the following detailed description, drawings and claims.

BRIEF DESCRIPTION OF THE FIGURES

FIGS. 1A, 1B, and 1C show that CD80-transfected human tumor cells co-express both CD80 and PDL1. (A) Cutaneous melanoma C8161 and C8161/CD80 cells were stained for cell surface CD80 (i)(ii) and PDL1 (mAb 5H1) (iii) (iv), respectively and analyzed by flow cytometry. (B) Plasma membrane fractions of human tumor cells contain PDL1 and CD80. Plasma membrane fractions of lysates of PDL1-MEL1011, C8161, and C861/CD80 cells, and recombinant proteins (human TROY-Fc and PDL1-Fc) were electrophoresed by SDS-PAGE and western blotted with mAb to PDL1 (5H1) or -actin. (C) Treatment with PDL1 mAb 5H1 allows binding of PDL1 mAb 29E.2A3. C8161 and C8161/CD80 cells were incubated with unlabeled PDL1 mAb 5H1 (i) (ii), followed by staining with PDL1 mAb 29E.2A3 (iii) (iv), respectively and analysis by flow cytometry. Data are representative of 3, 2, and 3 independent experiments for (A), (B), and (C), respectively.

FIGS. 2A, 2B and 2C show that co-expression of CD80 on PDL1+ mouse tumor cells prevents binding of PD1. (A) CD80+ mouse tumor cells co-express PDL1. Mouse 4T1 and CD80-transfected 4T1 (4T1/CD80) mammary carcinoma cells were cultured −IFNγ and +IFNγ for 48 hrs and stained for PDL1 (mAb MIH5 (4T1 (a)(b)) and (4T1/CD80 (c) (d)), respectively, 10F.9G2 (4T1 (e)(f)) and (4T1/CD80 (g) (h)), and MIH6 (4T1 (i)(j)) and (4T1/CD80 (k) (l))) and CD80, and analyzed by flow cytometry. (B) CD80 prevents binding of PD1 to mouse PDL1+ tumor cells. 4T1 (i) (ii) and 4T1/CD80 (iii) (iv) cells were cultured with IFN for 48 hrs, followed by incubation±unlabeled PDL1 mAb 43H12, which disrupts PDL1-PD1 interactions. Tumor cells were subsequently incubated with recombinant mouse PD1-Fc followed by staining with APC-labeled mAb to PD1, and analyzed by flow cytometry. (C) CD80-transfected PDL1+ murine tumor cells restore activation of antigen-activated T cells. Splenocytes were isolated from DO11.10 transgenic mice and activated with OVA peptide in the presence of 4T1 or 4T1/CD80 murine mammary carcinoma cells. IFNγ production was measured by ELISA. Data are representative of 3 independent experiments.

FIGS. 3A, 3B and 3C show that soluble CD80 restores activation of CD4+ and CD8+ T lymphocytes. (A) PDL1+ C8161 human melanoma cells (left panel) (i) were cultured with PHA-activated healthy donor PBMC in the presence of sCD80-Fc or irrelevant fusion protein (sTROYFc) and IFNγ production measured by ELISA (right panel) (ii). (B) PDL1+ H292 bronchioloalveolar adenocarcinoma cells (left panel) (i) were cultured with PHA-activated healthy donor PBMC in the presence of sCD80-Fc or irrelevant fusion protein (sTROYFc) and IFNγ production measured by ELISA (right panel) (ii), H358 squamous cell carcinoma cells (left panel) (iii) were cultured with PHA-activated healthy donor PBMC in the presence of sCD80-Fc or irrelevant fusion protein (sTROYFc) and IFNγ production measured by ELISA (right panel) (iv), and MCF10 mammary carcinoma cells (left panel) (v) were cultured with PHA-activated healthy donor PBMC in the presence of sCD80-Fc or irrelevant fusion protein (sTROYFc) and IFNγ production measured by ELISA (right panel) (iv) were cultured as in panel (A). (C) Healthy donor PBMC were undepleted (i), CD8-depleted (ii), CD4-depleted (iii), or CD8 and CD4-depleted (iv) prior to PHA activation and subsequent incubation with C8161 human melanoma cells as in (A). Data are representative of 3, 2, and 2 independent experiments for (A), (B), and (C), respectively.

DETAILED DESCRIPTION OF THE INVENTION

Figure 1C:
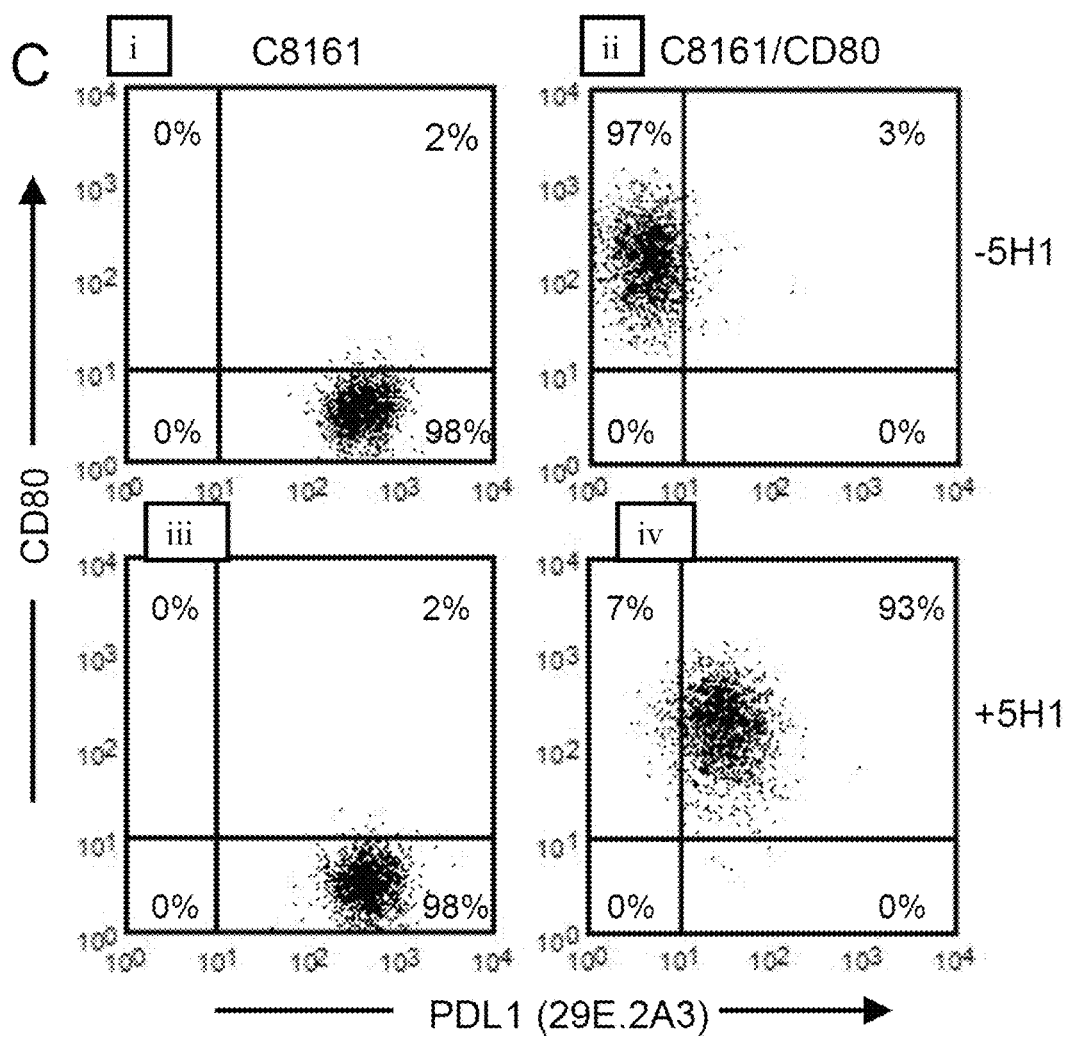

The present invention is based on the discovery of a previously unknown function for the CD80 costimulatory molecule that binds to PDL1, that being, the use of soluble CD80 as a novel immunotherapeutic strategy for diminishing immune suppression in cancer patients. The present invention provides for a soluble chimeric polypeptide comprising at least two extracellular domain of human CD80 fused to the Fc region of human IgG1 (sCD80-Fc) that forms a complex capable of binding to PDL1. Accordingly, chimeric polypeptides or a nucleic acid encoding the chimeric polypeptides of the present invention can be used therapeutically for inhibiting, preventing or reducing PDL-1 mediated immune suppression.

In order to facilitate review of the various embodiments of the invention and provide an understanding of the various elements and constituents used in making and using the present invention, the following terms used in the invention description have the following meanings.

As used herein, the terms "polypeptide," "protein" and "peptide" are used interchangeably to denote a sequence polymer of at least two amino acids covalently linked by an amide bond, regardless of length or post-translational modification (e.g., glycosylation, phosphorylation, lipidation, myristilation, ubiquitination, etc.). D-and L-amino acids, and mixtures of D-and L-amino acids are also included.

Chimeric polypeptide refers to an amino acid sequence having two or more parts which generally are not found together in an amino acid sequence in nature.

The term "spacer/linker" as used herein refers to a molecule that connects two monomeric protein units to form a chimeric molecule and still provides for binding of the soluble chimeric molecule to PD-L1. Particular examples of spacer/linkers may include an amino acid spacer, wherein thee amino acid sequence can essentially be any length, for example, as few as 5 or as many as 200 or more preferably from about 5 to 30 amino acid residues.

The term "therapeutic," as used herein, means a treatment administered to a subject who exhibits signs of pathology for the purpose of diminishing or eliminating those signs.

The term "therapeutically effective amount," as used herein means an amount of the chimeric protein that is sufficient to provide a beneficial effect to the subject to which the chimeric protein is administered. A beneficial effect means inhibiting or reducing PDL1-mediated suppression by human tumor cells by inhibiting PDL1-PD1 interations.

Thus, in accordance with the present invention, chimeric polypeptides, including truncated or internally deleted sequences, are provided. In one embodiment, the CD80 protein sequence may include one or more amino acids removed in comparison to their corresponding full-length polypeptide sequence.

Another example of a modification is the addition of a heterologous domain that imparts a distinct functionality upon the chimeric polypeptide. A heterologous domain can be any small organic or inorganic molecule or macromolecule, so long as it imparts an additional function. Particular examples of heterologous domains that impart a distinct function include an amino acid sequence that imparts targeting (e.g., receptor ligand, antibody, etc.), immunopotentiating function (e.g., immunoglobulin, an adjuvant), enable purification, isolation or detection (e.g., myc, T7 tag, polyhistidine, avidin, biotin, lectins, etc.).

As exemplified herein, polypeptide sequences may include substitutions, variations, or derivitizations of the amino acid sequence of one or both of the polypeptide sequences that comprise the chimeric polypeptide, so long as the modified chimeric polypeptide has substantially the same activity or function as the unmodified chimeric polypeptide. For example, the CD80 polypeptide sequence may have carbohydrates, fatty acids (palmitate, myristate), lipids, be phosphorylated or have other post-translational modifications typically associated with polypeptide sequences.

As used herein, the term "substantially the same activity or function," when used in reference to a chimeric polypeptide so modified, means that the polypeptide retains most, all or more of the activity associated with the unmodified polypeptide, as described herein or known in the art. Similarly, modifications that do not affect the ability of chimeric polypeptide to interact with PDL-1 are included herein.

Modified chimeric polypeptides that are "active" or "functional" included herein can be identified through a routine functional assay. For example, by using antibody binding assays or co-receptor binding assays one can readily determine whether the modified chimeric polypeptide has activity.

As the modified chimeric polypeptides will retain activity or function associated with unmodified chimeric polypeptide, modified chimeric polypeptides will generally have an amino acid sequence "substantially identical" or "substantially homologous" with the amino acid sequence of the unmodified polypeptide. As used herein, the term "substantially identical" or "substantially homologous," when used in reference to a polypeptide sequence, means that a sequence of the polypeptide is at least 50% identical to a reference sequence. Modified polypeptides and substantially identical polypeptides will typically have at least 70%, alternatively 85%, more likely 90%, and most likely 95% homology to a reference polypeptide.

As set forth herein, substantially identical or homologous polypeptides include additions, truncations, internal deletions or insertions, conservative and non-conservative substitutions, or other modifications located at positions of the amino acid sequence which do not destroy the function of the chimeric polypeptide (as determined by functional assays, e.g., as described herein). A particular example of a substitution is where one or more amino acids is replaced by another, chemically or biologically similar residue. As used herein, the term "conservative substitution" refers to a substitution of one residue with a chemically or biologically similar residue. Examples of conservative substitutions include the replacement of a hydrophobic residue, such as isoleucine, valine, leucine, or methionine for another, the replacement of a polar residue for another, such as the substitution of arginine for lysine, glutamic for aspartic acids, or glutamine for asparagine, and the like. Those of skill in the art will recognize the numerous amino acids that can be modified or substituted with other chemically similar residues without substantially altering activity.

Modified polypeptides further include "chemical derivatives," in which one or more of the amino acids therein have a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters; free hydroxyl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, and so forth. Also included are D-amino acids and amino acid derivatives that can alter covalent bonding, for example, the disulfide linkage that forms between two cysteine residues that produces a cyclized polypeptide.

As used herein, the terms "isolated" or "substantially pure," when used as a modifier of invention chimeric polypeptides, sequence fragments thereof, and polynucleotides, means that they are produced by human intervention and are separated from their native in vivo—cellular environment. Generally, polypeptides and polynucleotides so separated are substantially free of other proteins, nucleic acids, lipids, carbohydrates or other materials with which they are naturally associated.

Polypeptides, that being CD80 of the present invention may be prepared by standard techniques well known to those skilled in the art. Such techniques include, but are not limited to, isolation and purification from tissues known to contain that polypeptide, and expression from cloned DNA that encodes such a polypeptide using transformed cells. Chimeric polypeptides can be obtained by expression of a polynucleotide encoding the polypeptide in a host cell, such as a bacteria, yeast or mammalian cell, and purifying the expressed chimeric polypeptide by purification using typical biochemical methods (e.g., immunoaffinity purification, gel purification, expression screening etc). Other well-known methods are described in Deutscher et al., (Guide to Protein Purification: Methods in Enzymology, Vol. 182, Academic Press (1990), which is incorporated herein by reference). Alternatively, the chimeric polypeptide can be chemically synthesized. Purity can be measured by any appropriate method, e.g., polyacrylamide gel electrophoresis, and subsequent staining of the gel (e.g., silver stain) or by HPLC analysis.

The present invention further provides polynucleotide sequences encoding chimeric polypeptides, fragments thereof, and complementary sequences. As used herein, the terms "nucleic acid," "polynucleotide," "oligonucleotide," and "primer" are used interchangeably to refer to deoxyribonucleic acid (DNA) or ribonucleic (RNA), either double- or single-stranded, linear or circular. RNA can be unspliced or spliced mRNA, rRNA, tRNA, or antisense RNAi. DNA can be complementary DNA (cDNA), genomic DNA, or an antisense. Specifically included are nucleotide analogues and derivatives, such as those that are resistant to nuclease degradation, which can function to encode an invention chimeric polypeptide. Nuclease resistant oligonucleotides and polynucleotides are particularly useful for the present nucleic acid vaccines described herein.

An "isolated" or "substantially pure" polynucleotide means that the nucleic acid is not immediately contiguous with the coding sequences with either the 5' end or the 3' end with which it is immediately contiguous in the naturally occurring genome of the organism from which it is derived. The term therefore includes, for example, a recombinant DNA (e.g., a cDNA or a genomic DNA fragment produced by PCR or restriction endonuclease treatment produced during cloning), as well as a recombinant DNA incorporated into a vector, an autonomously replicating plasmid or virus, or a genomic DNA of a prokaryote or eukaryote.

The polynucleotides sequences of the present invention can be obtained using standard techniques known in the art (e.g., molecular cloning, chemical synthesis) and the purity can be determined by polyacrylamide or agarose gel electrophoresis, sequencing analysis, and the like. Polynucleotides also can be isolated using hybridization or computer-based techniques that are well known in the art. Such techniques include, but are not limited to: (1) hybridization of genomic DNA or cDNA libraries with probes to detect homologous nucleotide sequences; (2) antibody screening of polypeptides expressed by DNA sequences (e.g., using an expression library); (3) polymerase chain reaction (PCR) of genomic DNA or cDNA using primers capable of annealing to a nucleic acid sequence of interest; (4) computer searches of sequence databases for related sequences; and (5) differential screening of a subtracted nucleic acid library.

The invention also includes substantially homologous polynucleotides. As used herein, the term "homologous," when used in reference to nucleic acid molecule, refers to similarity between two nucleotide sequences. When a nucleotide position in both of the molecules is occupied by identical nucleotides, then they are homologous at that position. "Substantially homologous" nucleic acid sequences are at least 50% homologous, more likely at least 75% homologous, and most likely 90% or more homologous. As with substantially homologous invention chimeric polypeptides, polynucleotides substantially homologous to invention polynucleotides encoding chimeric polypeptides encode polypeptides that retain most or all of the activity or function associated with the sequence to which it is homologous. For polynucleotides, the length of comparison between sequences will generally be at least 30 nucleotides, alternatively at least 50 nucleotides, more likely at least 75 nucleotides, and most likely 110 nucleotides or more. Algorithms for identifying homologous sequences that account for polynucleotide sequence gaps and mismatched oligonucleotides are known in the art, such as BLAST (see, e.g., Altschul et al., J. Mol. Biol. 15:403-10 (1990)).

The polynucleotides of the present invention can, if desired: be naked or be in a carrier suitable for passing through a cell membrane (e.g., polynucleotide-liposome complex or a colloidal dispersion system), contained in a vector (e.g., retrovirus vector, adenoviral vectors, and the like), linked to inert beads or other heterologous domains (e.g., antibodies, ligands, biotin, streptavidin, lectins, and the like), or other appropriate compositions disclosed herein or known in the art. Thus, viral and non-viral means of polynucleotide delivery can be achieved and are contemplated. The polynucleotides of the present invention can also contain additional nucleic acid sequences linked thereto that encode a polypeptide having a distinct functionality, such as the various heterologous domains set forth herein.

The polynucleotides of the present invention can also be modified, for example, to be resistant to nucleases to enhance their stability in a pharmaceutical formulation. The described polynucleotides are useful for encoding chimeric polypeptides of the present invention, especially when such polynucleotides are incorporated into expression systems disclosed herein or known in the art. Accordingly, polynucleotides including an expression vector are also included.

For propagation or expression in cells, polynucleotides described herein can be inserted into a vector. The term "vector" refers to a plasmid, virus, or other vehicle known in the art that can be manipulated by insertion or incorporation of a nucleic acid. Such vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Control elements, including promoters present within an expression vector, are included to facilitate proper transcription and translation (e.g., splicing signal for introns, maintenance of the correct reading frame of the gene to permit in-frame translation of mRNA and stop codons). In vivo or in vitro expression of the polynucleotides described herein can be conferred by a promoter operably linked to the nucleic acid.

"Promoter" refers to a minimal nucleic acid sequence sufficient to direct transcription of the nucleic acid to which the promoter is operably linked (see, e.g., Bitter et al., Methods in Enzymology, 153:5 16-544 (1987)). Promoters can constitutively direct transcription, can be tissue-specific, or can render inducible or repressible transcription; such elements are generally located in the 5' or 3' regions of the gene so regulated.

As used herein, the term "operably linked" means that a selected polynucleotide (e.g., encoding a chimeric polypeptide) and regulatory sequence(s) are connected in such a way as to permit transcription when the appropriate molecules (e.g., transcriptional activator proteins) are bound to the regulatory sequence(s). Typically, a promoter is located at the 5' end of the polynucleotide and may be in close proximity of the transcription initiation site to allow the promoter to regulate expression of the polynucleotide.

When cloning in bacterial systems, constitutive promoters, such as T7 and the like, as well as inducible promoters, such as pL of bacteriophage gamma, plac, ptrp, ptac, may be used. When cloning in mammalian cell systems, constitutive promoters, such as SV40, RSV and the like, or inducible promoters derived from the genome of mammalian cells (e.g., the metallothionein promoter) or from mammalian viruses (e.g., the mouse mammary tumor virus long terminal repeat, the adenovirus late promoter), may be used. Promoters produced by recombinant DNA or synthetic techniques may also be used to provide for transcription of the nucleic acid sequences of the invention.

Mammalian expression systems that utilize recombinant viruses or viral elements to direct expression may be engineered. For example, when using adenovirus expression vectors, the nucleic acid sequence may be ligated to an adenovirus transcription/translation control complex, e.g., the late promoter and tripartite leader sequence. Alternatively, the vaccinia virus 7.5K promoter may be used (see, e.g., Mackett et al., Proc. Natl. Acad. Sci. USA, 79:7415-7419 (1982); Mackett et al., J. Virol., 49:857-864 (1984); Panicali et al., Proc. Natl. Acad. Sci. USA, 79:4927-4931 (1982)).

For yeast expression, a number of vectors containing constitutive or inducible promoters may be used (see, e.g., Current Protocols in Molecular Biology, Vol. 2, Ch. 13, ed. Ausubel et al., Greene Publish. Assoc. & Wiley Interscience (1988); Grant et al., "Expression and Secretion Vectors for Yeast," in Methods in Enzymology, Vol. 153, pp. 516-544, eds. Wu & Grossman, 3 1987, Acad. Press, N.Y. (1987); Glover, DNA Cloning, Vol. II, Ch. 3, IRL Press, Wash., D.C. (1986); Bitter, "Heterologous Gene Expression in Yeast," Methods in Enzymology, Vol. 152, pp. 673-684, eds. Berger & Kimmel, Acad. Press, N.Y. (1987); and The Molecular Biology of the Yeast *Saccharomyces*, eds. Strathem et al., Cold Spring Harbor Press, Vols. I and II (1982)). The polynucleotides may be inserted into an expression vector for expression in vitro (e.g., using in vitro transcription/translation kits, which are available commercially), or may be inserted into an expression vector that contains a promoter sequence that facilitates expression in either prokaryotes or eukaryotes by transfer of an appropriate nucleic acid into a suitable cell, organ, tissue, or organism in vivo.

As used herein, a "transgene" is any piece of a polynucleotide inserted by artifice into a host cell, and becomes part of the organism that develops from that cell. A transgene can include one or more promoters and any other DNA, such as introns, necessary for expression of the selected DNA, all operably linked to the selected DNA, and may include an enhancer sequence. A transgene may include a polynucleotide that is partly or entirely heterologous (i.e., foreign) to the transgenic organism, or may represent a gene homologous to an endogenous gene of the organism. Transgenes may integrate into the host cell's genome or be maintained as a self-replicating plasmid.

As used herein, a "host cell" is a cell into which a polynucleotide is introduced that can be propagated, transcribed, or encoded polypeptide expressed. The term also includes any progeny of the subject host cell. It is understood that all progeny may not be identical to the parental cell, since there may be mutations that occur during replication. Host cells include but are not limited to bacteria, yeast, insect, and mammalian cells. For example, bacteria transformed with recombinant bacteriophage polynucleotide, plasmid nucleic acid, or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV), or transformed with recombinant plasmid expression vectors (e.g., Ti plasmid), insect cell systems infected with recombinant virus expression vectors (e.g., baculovirus), or animal cell systems infected with recombinant virus expression vectors (e.g., retroviruses, adenovirus, vaccinia virus), or transformed animal cell systems engineered for stable expression.

As used herein, the term "transformation" means a genetic change in a cell following incorporation of a polynucleotide (e.g., a transgene) exogenous to the cell. Thus, a "transformed cell" is a cell into which, or a progeny of which, a polynucleotide has been introduced by means of recombinant techniques. Transformed cells do not include an entire human being. Transformation of a host cell may be carried out by conventional techniques known to those skilled in the art. When the host cell is a eukaryote, methods of DNA transformation include, for example, calcium phosphate, microinjection, electroporation, liposomes, and viral vectors. Eukaryotic cells also can be co-transformed with invention polynucleotide sequences or fragments thereof, and a second DNA molecule encoding a selectable marker, as described herein or otherwise known in the art. Another method is to use a eukaryotic viral vector, such as simian virus 40 (SV40) or bovine papilloma virus, to transiently infect or transform eukaryotic cells, and express the protein (see, e.g., Eukaryotic Viral Vectors, Cold Spring Harbor Laboratory, Gluzman ed. (1982)). When the host is prokaryotic (e.g., E. coli), competent cells that are capable of DNA uptake can be prepared from cells harvested after exponential growth phase and subsequently treated by the CaCl2 method using procedures well-known in the art. Transformation of prokaryotes also can be performed by protoplast fusion of the host cell.

Chimeric polypeptides, polynucleotides, and expression vectors containing same of the present invention can be encapsulated within liposomes using standard techniques and introduced into cells or whole organisms. Cationic liposomes are preferred for delivery of polynucleotides. The use of liposomes for introducing various compositions in vitro or in vivo, including proteins and polynucleotides, is known to those of skill in the art.

Liposomes can be targeted to a cell type or tissue of interest by the addition to the liposome preparation of a ligand, such as a polypeptide, for which a corresponding cellular receptor has been identified. Monoclonal antibodies can also be used for targeting; many such antibodies specific for a wide variety of cell surface proteins are known to those skilled in the art and are available. The selected ligand is covalently conjugated to a lipid anchor in either preformed liposomes or are incorporated during liposome preparation (see Lee & Low, J Biol. Chem., 269:3 198 (1994); Lee & Low Biochem. Biophys. Actu, 1233: 134 (1995)).

As the chimeric polypeptides or polynucleotides of the present invention will be administered to humans, the present invention also provides pharmaceutical formulations comprising the disclosed chimeric polypeptides or polynucleotides. The compositions administered to a subject will therefore be in a "pharmaceutically acceptable" or "physiologically acceptable" formulation.

As used herein, the terms "pharmaceutically acceptable" and "physiologically acceptable" refer to carriers, diluents, excipients, and the like that can be administered to a subject, preferably without excessive adverse side effects (e.g., nausea, headaches, etc.). Such preparations for administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions, or suspensions, including saline and buffered media. Vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present, such as, for example, antimicrobial, anti-oxidants, chelating agents, and inert gases and the like. Various pharmaceutical formulations appropriate for administration to a subject known in the art are applicable in the methods of the invention (e.g., Remington's Pharmaceutical Sciences, 18th ed., Mack Publishing Co., Easton, Pa. (1990); and The Merck Index, 12th ed., Merck Publishing Group, Whitehouse, N.J. (1996)).

Controlling the duration of action or controlled delivery of an administered composition can be achieved by incorporating the composition into particles or a polymeric substance, such as polyesters, polyamine acids, hydrogel, polyvinyl pyrrolidone, ethylene-vinylacetate, methylcellulose, carboxymethylcellulose, protamine sulfate or lactide/glycolide copolymers, polylactide/glycolide copolymers, or ethylenevinylacetate copolymers. The rate of release of the composition may be controlled by altering the concentration or composition of such macromolecules. Colloidal dispersion systems include macromolecule complexes, nano-capsules, microspheres, beads, and lipid-based systems, including oil-in-water emulsions, micelles, mixed micelles, and liposomes.

The compositions administered by a method of the present invention can be administered parenterally by injection, by gradual perfusion over time, or by bolus administration or by a microfabricated implantable device. The composition can be administered via inhalation, intravenously, intraperitoneally, intramuscularly, subcutaneously, intracavity (e.g., vaginal or anal), transdermally, topically, or intravascularly. The compositions can be administered in multiple doses. An effective amount can readily be determined by those skilled in the art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Other features and advantages of the invention will be apparent from the following detailed description, and from the claims. The invention is further described in the following examples, which do not limit the scope of the invention(s) described in the claims.

EXAMPLES

Materials and Methods
Cell Lines, Plasmids, and Transfections
Human cutaneous melanoma cell lines MEL1011 and C8161, mammary carcinoma MCF10CA1 (hereafter called MCF10), bronchioloalveolar adenocarcinoma H358, squamous cell carcinoma H292, and mouse BALB/c-derived mammary carcinoma 4T1 cells were cultured as described (22-24). MCF10/DR7, C8161/CD80, and 4T1/CD80 transfectants were generated and maintained as described (22, 24, 25). Cell lines and procedures with human and mouse materials were approved by the UMBC Institutional Review Board and Institutional Animal Care and Use Committee, respectively.

Construction of the CD80-Fc Fusion Protein

Expression plasmid encoding the CD80 signal and extacellular domains (SEQ ID NO: 4) fused to the Fc section of human IgG1 (SEQ ID NO: 8) were constructed as follows: cDNA encoding the signal and extracellular domains of human CD80 (SEQ ID NO: 1) was generated by PCR amplification from full-length cDNA commercially available. The cDNA extends from immediately after the Met in the signal sequence through $Asp^{241}$ of the total protein sequence. Primary PCR of CD80 was done with the 5' and 3' primers: Forward CD80: 5' GCG CGG ATC CGG CCA CAC ACG GAG G 3' (SEQ NO: 2) Reverse CD80: 5' GAG TTT TGT CAT TTA CTG AGA TTA AG 3' (SEQ ID NO: 3), The Fc gene portion of the IgG1 (SEQ ID NO: 5) was PCR amplified with 5' primer and 3' primer; forward primer 5'-CTC AGT AAA TGA CAA AAC TCA CAC A-3' (SEQ ID NO: 6) and reverse primer is 5'-GCG CAA GCT TTT AGT GAT GGT GAT GGT GAT GTT TAC CCG GAG ACA G-3' (SEQ ID NO: 7). The CF80-Fc gene was inserted into a pet21a+ vector (Novagen) and expressed in bacteria cells. The expressed fusion protein, including SEQ ID NOs 4 and 8, was purified from the culture medium by chromatography.

Western Blots

Western blots were performed as described (26) with the following modifications. Tumor cells were washed twice with sterile PBS. $1\times10^7$ tumor cells were resuspended in 800 ul PBS and homogenized using a GentleMACS Dissociator in GentleMACS M tubes (Miltenyi Biotec, Auburn, Calif.). Homogenized tumor cells were centrifuged at 13,690×g (Jouan, Winchester, Va.) at 4° C. for 30 min. Supernatants containing the cytoplasmic proteins were discarded, 150 ul ice-cold lysis buffer was added to the pellets containing the membrane proteins, and the mixture incubated at 4° C. for 30 min on an Eppendorf Mixer (Eppendorf Mixer 5432). The resulting lysates were centrifuged at 13,690×g at 4° C. for 30 min, and the supernatants were resuspended in sample buffer (0.5M Tris ph 6.8, Glycerol, 20% SDS, H20, and bromophenol blue). Lysates were electrophoresed on 12% SDS-PAGE gels, proteins transferred to polyvinylidene difluoride membranes (Amersham, Piscataway, N.J.) using a Bio-Rad PowerPac HC (100 V for 70 min), and the membranes blocked with 5% nonfat dry milk in Tris-buffered saline and Tween 20 (TBST). PDL1 and β-actin were detected using 1 ug/ml PDL1 mAb (clone 5H1 (1)) and 0.05 ug/ml β-actin mAb, respectively, followed by 1:5000 dilution of goat anti-mouse HRP (BD Biosciences, San Jose, Calif.).

Mice

Breeding stock for BALB/c and BALB/c T cell receptor transgenic DO11.10 (I-$A^d$-restricted, OVA peptide 323-339-specific) mice were from The Jackson Laboratory. Mice were bred and maintained in the UMBC animal facility. All animal procedures were approved by the UMBC Institutional Animal Care and Use Committee.

Antibodies, Reagents, and Flow Cytometry

Human CD80-FITC (clone L307.4), mouse CD80-FITC (clone 16-10A1), mouse PDL1-PE (clone MIH5), human CTLA4-PE (clone BNI3), mouse IgG1-FITC (clone X40), rat IgG$_{2a}$-PE (clone R35-95), and hamster IgG-FITC (clone UC8-4B3) monoclonal antibodies (mAb) were from BD Biosciences. Human PDL1-APC (clone 29E.2A3), mouse PDL1-PE (clone 10F.9G2), human CD28-FITC (clone CD28.2), and rat IgG$_{2a}$AlexaFluor647 (clone RTK2758) were from BioLegend (San Diego, CA). Mouse PDL1(clone MIH6), mouse IgG$_{2b}$-APC (clone eBMG2b), and rat IgG$_{2b}$-PE (clone TER-119) were from AbD Serotec (Raleigh, NC), eBioscience (San Diego, CA), and Caltag (Burlingame, CA), respectively. OVA323-339 peptide (ISQAVHAAHAEINEAGR) (SEQ ID NO. 16) was synthesized in the Biopolymer Core Facility at the University of Maryland, Baltimore. Cells were stained for cell surface expression and subjected to flow cytometry as described (26, 27), and analyzed using a Beckman Coulter Cyan ADP flow cytometer and Summit V4.3.02 software.

Human PBMC Activation

Cryopreserved PBMC were obtained from healthy human donors as described (28). PBMC ($6\times10^4$) and tumor cells (50 Gy-irradiated, $3\times10^4$) were co-cultured with 5 ug/ml PHA (Sigma-Aldrich, St. Louis, Mo.) at 37° C., 5% $CO_2$ for 72 hrs in a total volume of 200 µl T cell media (IMDM, human AB serum, glutamax, penicillin/streptomycin, gentamycin, sodium pyruvate, hepes buffer, β-mercaptoethanol, and prophylactic plasmocin) in 96 well plates. Human sCD80-Fc, human sPD1-Fc and human sTORY-Fc (TNF receptor superfamily member) fusion proteins (R&D Systems, Minneapolis, Minn.) were added to some wells at 10 µg/ml. Blocking mAb PDL1 (clone 29E.2A3) and PD1 (clone EH12.2H7) from BioLegend were used at 10 µg/ml. Purified anti-CD28 (clone CD28.2) from BioLegend was used at 1-4 µg/ml. CD4 and CD8 MicroBeads (Miltenyi) were used according to the manufacturer's directions to deplete PBMC of CD4+ and/or CD8+ T cells. Functional grade mouse IgG$_{2b}$ (clone eBMG2b) and IgG1 (clone P3.6.2.8.1) (eBioscience) were used at 10 µg/ml. Molar equivalence of anti-CD28 and sCD80-Fc: 0.01 µM anti-CD28=1.5 µg/ml; 0.01 µM sCD80-Fc=0.26 µg/ml. IFN production was measured by ELISA (28).

IFN-γ Treatment and Soluble PD1-Fc Binding

4T1 and 4T1/CD80 cells were incubated at 37° C. for 48 hrs in their culture medium supplemented with 100 U/ml recombinant mouse IFN-γ (Pierce-Endogen, Rockford, Ill.), washed with excess culture medium, and subsequently incubated in the presence or absence of mouse PDL1 (clone 43H12 (5)), followed by incubation with recombinant mouse PD1-Fc fusion protein and anti-mouse PD1-APC (BioLegend).

Mouse Splenocyte Activation

Splenocytes from DO11.10 mice were depleted of red blood cells and cultured at 37 C 5% CO2 in 96-well plates at 105 cells/well with 2 ug/well OVA peptide 323-339 in a total volume of 100 l/well. After 48 hrs 100 µl containing 2×105 irradiated (100 Gy) 4T1 or 4T1/CD80 cells were added per well and the cultures incubated at 37 C, 5% CO2 for an additional 48 hrs. IFN production was measured by ELISA (BioLegend).

Statistical Analysis

Standard deviation and Student's t test were utilized using Excel version 2008. Mann-Whitney test was performed using software available from Vassar.

Example 1

CD80 Prevents Binding of Some PDL1 mAb to CD80+PDL1+ Human Tumor Cells

It has been previously reported that PDL1 was not detected on the cell surface of CD80– transfected PDL1+ human tumor cells (22). These studies used three anti-PDL1 mAb and raised the question of whether CD80 prevents expression or obstructs detection of cell surface PDL1. To resolve this issue, an additional anti-PDL1 mAb was used in flow cytometry and western blot experiments. C8161 and CD80-transfected C8161 (C8161/CD80) cells were stained for CD80 and PDL1 using the mAb 5H1 (1) and analyzed by flow cytometry, as shown in FIG. 1A. In contrast to previous findings with the anti-PDL1 mAb, that being 29E.2A3, MIH1, and 27A2 mAb, the newly used 5H1 mAb stained C8161/CD80 cells at levels comparable to parental C8161 cells, indicating that CD80 does not inhibit cell surface expression of PDL1. To confirm that CD80+ cells contain cell surface PDL1, C8161 and C8161/CD80 cells were lysed and the lysates enriched for cell membranes and subjected to western blotting with mAb 5H1, as shown in FIG. 1B. Soluble CD80-Fc (sCD80-Fc) and C8161 cells served as positive controls. MEL1011, a PDL1-cell line, and soluble TROY-Fc (sTROY-Fc), an irrelevant soluble protein, were negative controls. C8161 and C8161/CD80 cells contain similar levels of membrane PDL1, confirming that CD80 does not obstruct cell surface expression of PDL1.

Previous studies failed to detect cell surface PDL1 on C8161/CD80 cells and five other human tumor cell lines, using the anti-PDL1 mAb 29E.2A3, MIH1, and 27A2 (22). These mAbs may have failed to detect PDL1 because they recognized epitopes that were sterically blocked by CD80. Tamada and colleagues have generated a rat anti-mouse PDL1 mAb (43H12) that prevents the binding of mouse CD80 to mouse PDL1 (5). Since 5H1 detects PDL1 on PDL1+CD80+ human cells, it was theorized that it may have the same effect on human CD80-PDL1 interactions as 43H12 has on mouse cells. To test this possibility C8161 and C8161/CD80 cells were either untreated or pre-treated with the 5H1 mAb prior to labeling with 29E.2A3 mAb, as shown in FIG. 1C. As previously observed, 29E.2A3 did not detect PDL1 on C8161/CD80 cells. However, if C8161/CD80 cells were pretreated with 5H1 mAb, then PDL1 was detected by 29E.A3 mAb. In contrast, pretreatment with 5H1 did not result in subsequent binding of anti-PDL1 mAb MIH1 or 27A2 (data not shown). These results demonstrate that PDL1 is present on the cell surface of CD80+ human tumor cells and that some mAbs do not detect it because their binding sites are sterically obstructed by CD80.

Example 2

Co-expression of CD80 and PDL1 on Mouse Tumor Cells Prevents PD1 Binding

Figure 2A:
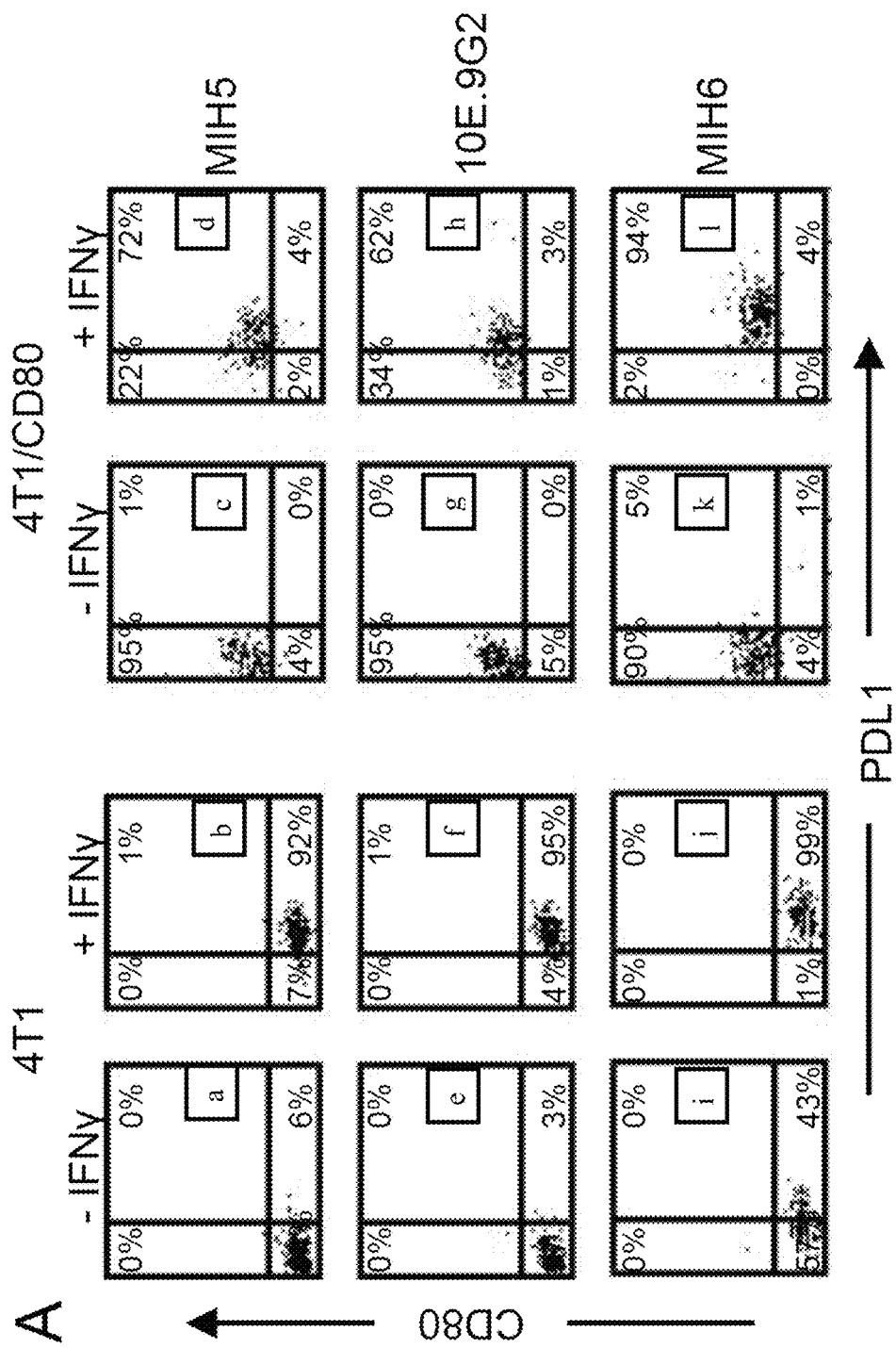

Previous studies established that co-expression of human CD80 on PDL1+ human tumor cells prevented PD1 binding and PDL1-mediated immune suppression (22). To determine if the same phenomenon occurred with murine cells, CD80−4T1 mammary carcinoma cells and their CD80 transfectants (4T1/CD80) were used. As is the case for human tumor cells, many mouse tumor cells constitutively express PDL1 and treatment with IFNγ increases PDL1 expression (29). Mouse tumor cells were cultured with or without IFNγ, then stained for CD80 and PDL1 using three mouse mAbs (MIH5, 10E.9G2, and MIH6), and subsequently analyzed by flow cytometry, as shown in FIG. 2A. IFNγ up-regulated cell surface PDL1 expression on both 4T1 and 4T1/CD80 cells and all three mAbs detected PDL1 on 4T1/CD80 cells. These results indicated that unlike the situation with human tumor cells, mAb to mouse PDL1 predominantly react with epitopes outside of the mouse CD80-PDL1 binding region.

To determine if co-expression of CD80 and PDL1 by mouse tumor cells prevents binding of mouse PD1, 4T1 and 4T1/CD80 cells were treated with IFNγ and subsequently incubated with or without a soluble form of PD1 (sPD1-Fc) followed by staining for PD1 and analysis by flow cytometry (FIG. 2B, top histograms). 4T1, but not 4T1/CD80 cells, bound sPD1-Fc, demonstrating that co-expression of mouse CD80 prevents PD1 binding as observed with human tumor cells.

To confirm that mouse CD80 prevents mouse PD1 binding by interacting with PDL1, the 43H12 mAb, which dissociates mouse CD80-PDL1 complexes, was used. (5) 4T1 and 4T1/CD80 cells were treated with IFNγ, followed by incubation with or without mAb 43H12, and subsequent staining with sPD1-Fc and anti-PD1-APC. The cells were then analyzed by flow cytometry (FIG. 2B, bottom histograms). sPD1-Fc bound to 4T1 cells but not 4T1/CD80 cells, and to both 4T1 and 4T1/CD80 cells following incubation with mAb 43H12, demonstrating that mouse CD80 prevents PD1-PDL1 interactions by binding to PDL1.

To determine if co-expression of mouse CD80 restores T cell activation in the presence of PDL1+ mouse tumor cells, 4T1 and 4T1/CD80 tumor cells were co-cultured with OVA peptide-activated splenocytes from DO11.10 mice transgenic for a T cell receptor specific for OVA peptide 323-339. T cell activation was assessed by measuring IFNγ production as shown in FIG. 2C. T cell activation was suppressed in the presence of PDL1+CD80− 4T1 cells, and there was no suppression in the presence of PDL1+CD80+4T1/CD80 cells. These results indicate that co-expression of CD80 inhibits PDL1-mediated immune suppression by both mouse and human tumor cells.

Example 3

Soluble CD80 Restores Activation of CD4+ and CD8+ T Lymphocytes

Figure 3B:
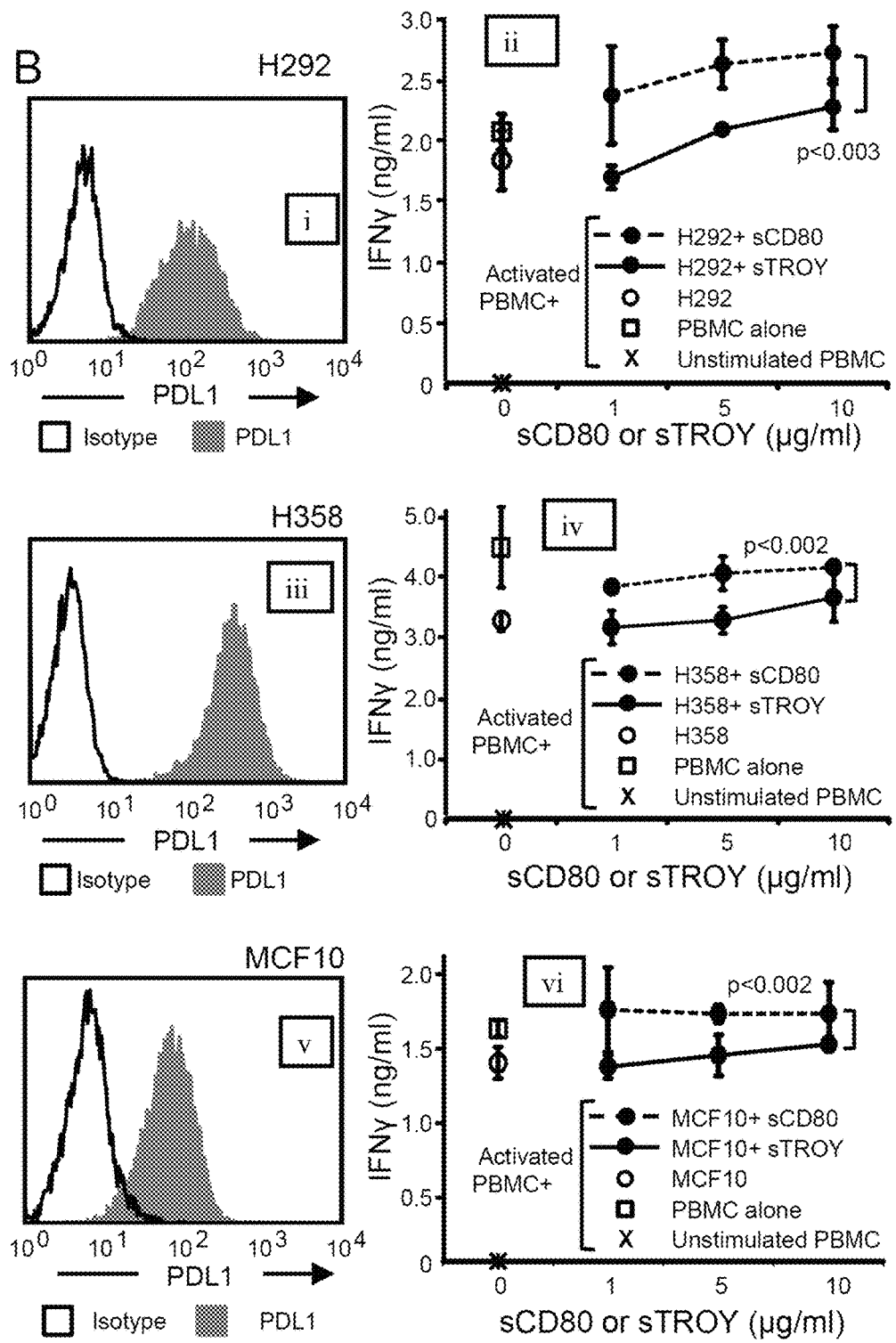

Membrane-bound CD80 prevents PDL1-PD1-mediated immune suppression by human tumor cells (22). However, introduction of membrane-bound CD80 into PDL1+ tumor cells is not an in vivo therapeutically feasible strategy. It was theorized that a soluble version of CD80 would have the same PDL1 binding properties as the membrane-bound form and therefore may also overcome PDL1 suppressive function. This hypothesis was tested using a fusion protein consisting of the extracellular two domains of human CD80 fused to the Fc domain of IgG1 (sCD80-Fc). The Fc domain of IgG1 was included to stabilize soluble CD80 (30). PDL1+ C8161 human melanoma cells were co-cultured with allogeneic human PBMC plus PHA in the presence or absence of tittered quantities of sCD80-Fc or an irrelevant control fusion protein (sTROY-Fc). PBMC activation was assessed by measuring IFNγ production, as shown in FIG. 3A. PDL1+C8161 cells suppressed IFNγ production by PHA-activated PBMC and inclusion of sCD80-Fc, but not sTORY-Fc, restored IFNγ production. sCD80-Fc similarly restored PBMC activation in the presence of PDL1+ human H292 squamous cell carcinoma, H358 bronchioloalveolar adenocarcinoma, and MCF10 breast cancer cells, as shown in FIG. 3B. To ascertain that sCD80-Fc was restoring activation of T lymphocytes, PBMC were depleted for CD4+, CD8+, or CD4+ plus CD8+ T cells prior to co-culture with PDL1+C8161 cells, PHA, and soluble fusion proteins (FIG. 3C). sCD80-Fc restored IFNγ production in undepleted cultures, while depletion of CD4+ T cells reduced IFNγ production, and depletion of CD4+ plus CD8+ T cells eliminated IFNγ production. These results demonstrate that sCD80-Fc restores activation of both CD4+ and CD8+ T cells.

Example 4 sCD80 Restores Activation More Effectively than mAb Against PD1 and PDL1

Figure 4:
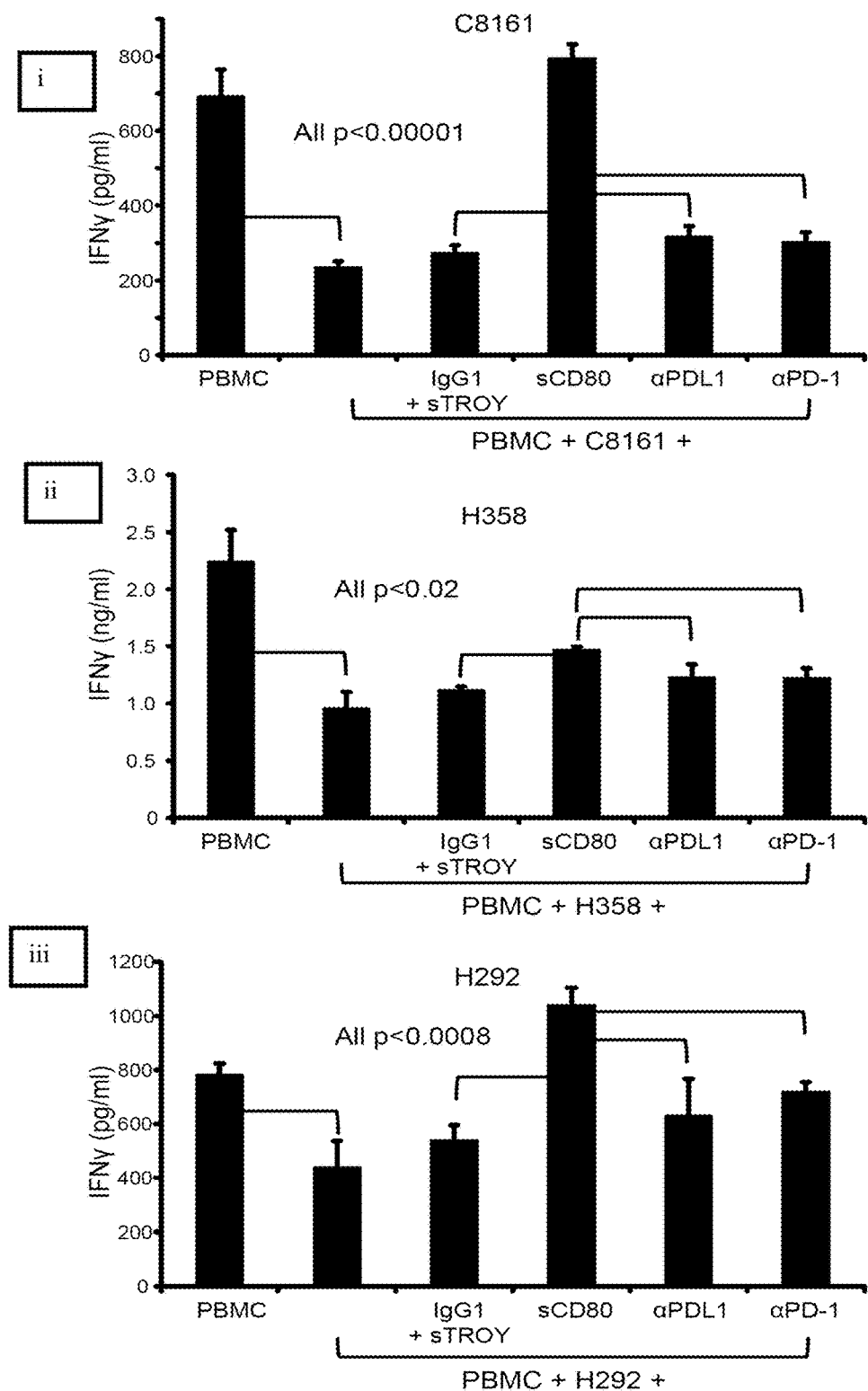
FIG. 4 shows that soluble CD80 restores PBMC activation more efficiently than antibodies to PDL1 or PD1. PHA-activated PBMC from healthy donors were co-cultured with human C8161 melanoma (i), H358 squamous cell carcinoma (ii), or H292 bronchioloalveolar adenocarcinoma (iii) cells in the presence of sCD80-Fc, antibodies to PD1 or PDL1, or control IgG1 plus irrelevant fusion protein sTROY-Fc. IFNγ production was measured by ELISA. Data are representative of 3 independent experiments for C8161, H358, and H292 cell lines.
Figure 6:
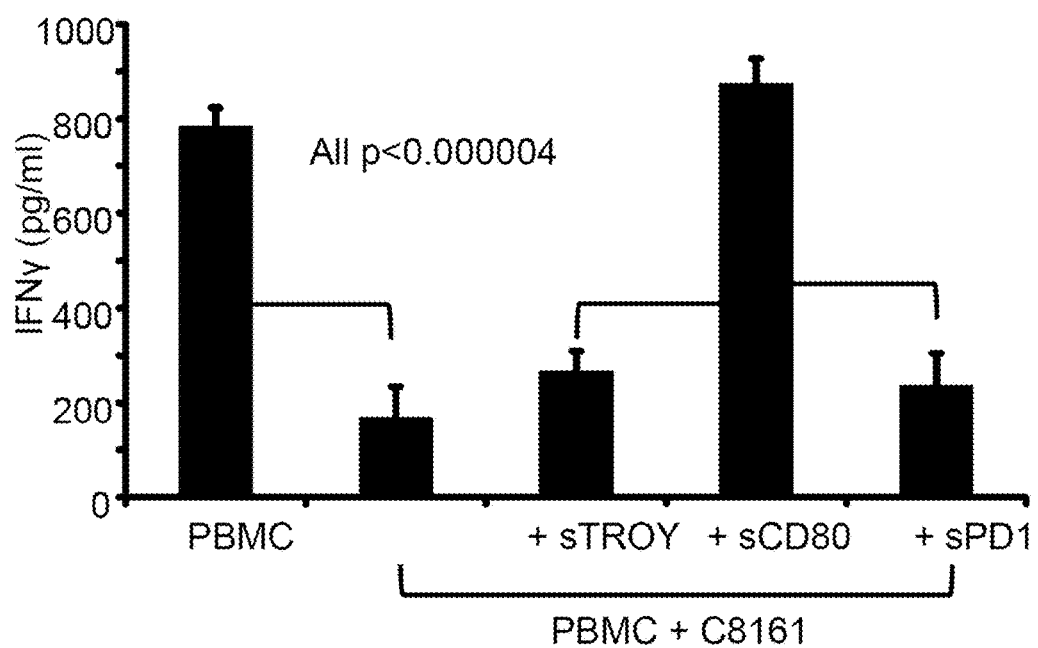
FIG. 6 shows that sCD80-Fc is more efficient than sPD1-Fc in preventing PDL1-PD1-mediated immune suppression. PBMC from healthy human donors were activated with PHA and incubated with C8161 human melanoma cells±soluble CD80-Fc, sPD1-Fc, or irrelevant fusion protein (sTROY-Fc). Data are representative of 3 independent experiments.

Antibodies to PDL1 and PD1 delayed tumor progression and improved anti-tumor immunity in mice (31, 32), and have shown clinical efficacy in extending survival time of some patients with melanoma, non-small cell lung cancer, and renal cell carcinoma (17, 18). To assess the relative activity of antibodies versus sCD80-Fc, PBMC were co-cultured with PHA and C8161, H358, or H292 cells in the presence or absence of equimolar binding units to CD28 of sCD80-Fc, sTROY-Fc, or antibodies to PDL1 or PD1. T cell activation was measured by IFNγ release, as shown in FIG. 4. T cell activation was suppressed and sCD80-Fc restored T cell activation and was more effective than antibodies to either PDL1 or PD1 for all three tumor cell lines. sCD80-Fc was similarly more effective than soluble PD1-Fc, as shown in FIG. 6.

Example 5 sCD80 Restores PBMC Activation by Neutralizing PDL1-PD1 Suppression

Figure 5A:
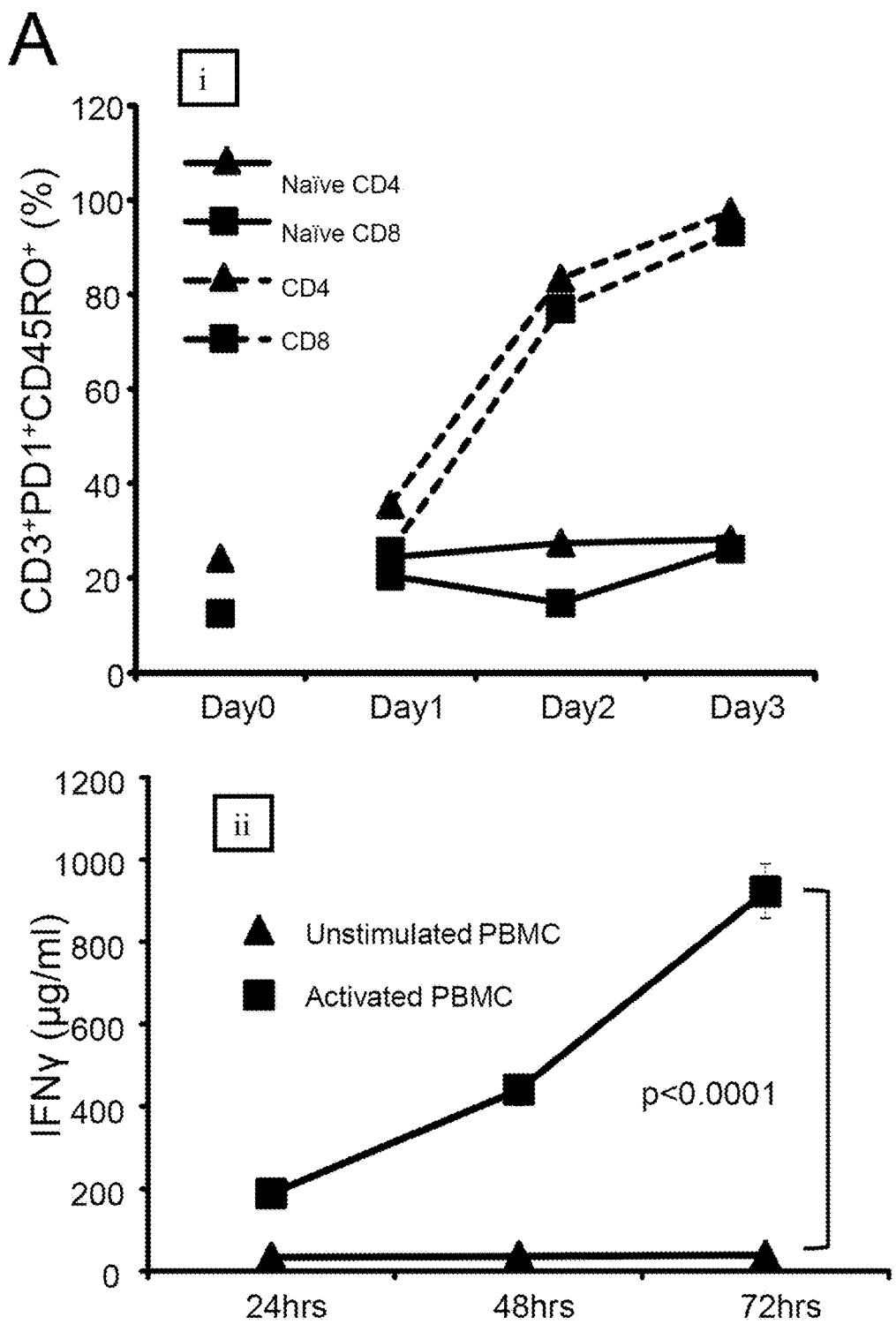
FIGS. 5A and 5B show that soluble CD80 restores PBMC activation by neutralizing PDL1-PD1 immune suppression. (A) PHA-activated PBMC express PD1. Healthy donor PBMC were PHA-activated and stained with mAb to PD1 (top panel) (i) on days 0-3, and supernatants assayed by ELISA for IFNγ (bottom panel) (ii) on days 1-3 post activation. (B) Healthy donor unstimulated PBMC ● were activated with PHA ▲ and cultured with antibodies to CD28 ♦ or soluble CD80 ■, IFNγ production was measured by ELISA. Molar concentration for antibody was ½ the molar concentration of sCD80-Fc to compensate for each antibody molecule binding two molecules of CD28 vs. each sCD80-Fc molecule binding only one molecule of CD28. Data are representative of 3 independent experiments.

If sCD80-Fc restores T cell activation by blocking PDL1-PD1 interactions, then activated T cells should express PD1. To confirm that PHA activation induces PD1 expression, human PBMC were cultured with PHA and tested for IFNγ production and expression of PD1 at 24, 48, and 72 hrs. Activated T cells were identified by their expression of CD3 plus CD4 or CD8, and the activation marker CD45RO (FIG. 5A). PD1 expression on activated T cells increased with time and in proportion to IFNγ production. These results indicate that PHA-activated T cells express PD1 and therefore should be susceptible to PDL1-mediated suppression.

Figure 5B:
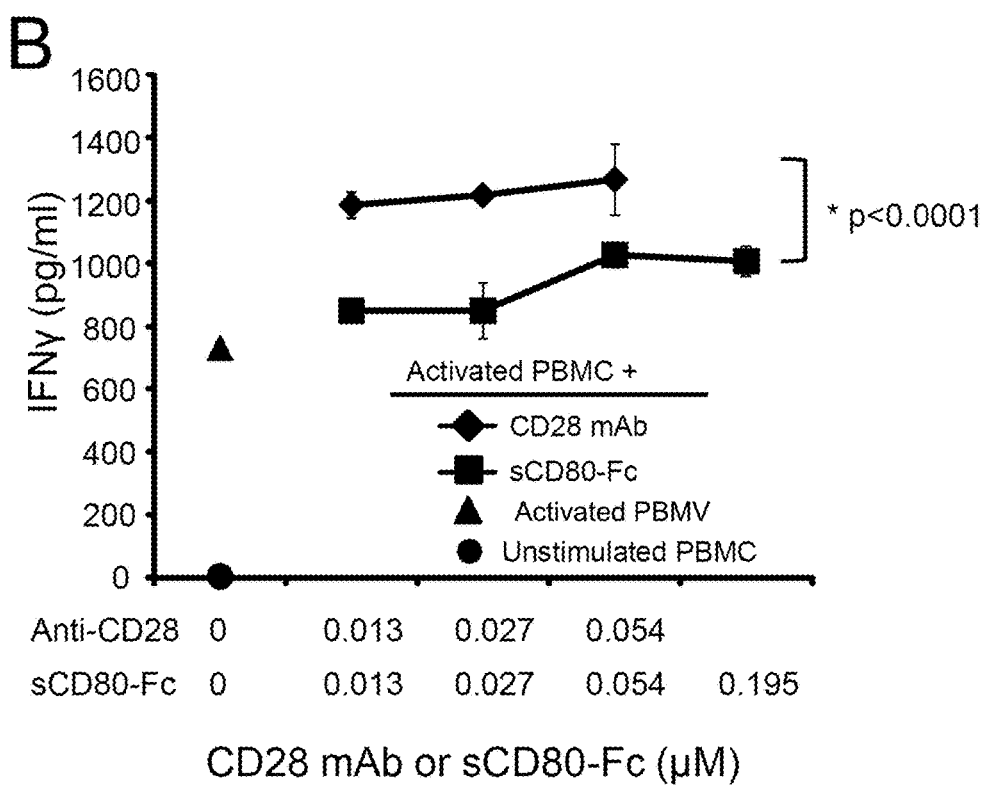

Previous studies conducted by the present inventors established that CD80 prevents PD1 binding to PDL1 (22). However, CD80 may also promote T cell activation by serving as a costimulatory signal to activate T cells through CD28 (33, 34). PHA-activated T cells express CD28, as shown in Figure, so they have the potential to be costimulated. To determine whether sCD80-Fc also costimulates, the ability of sCD80-Fc vs. antibodies to CD28 to boost the response of PHA-activated PBMC was compared in the absence of tumor cells. One anti-CD28 antibody binds two CD28 molecules, whereas one sCD80-Fc molecule binds only one CD28 molecule. To normalize binding capacity a comparison was made to compare the activity of two molar equivalents of sCD80-Fc vs. one molar equivalent of anti-CD28 mAb to increase the activation of PBMC in the presence of PHA (FIG. 5B). Antibodies to CD28 increased IFNγ production by 38-42%, whereas equal binding units of sCD80-Fc increased IFNγ production by 14-28% ($p<0.0001$). These results indicate that sCD80-Fc has limited costimulatory activity, and are consistent with the concept that sCD80-Fc increases T cell activation predominantly by inhibiting PDL1-PD1 interactions.

Figure 7:
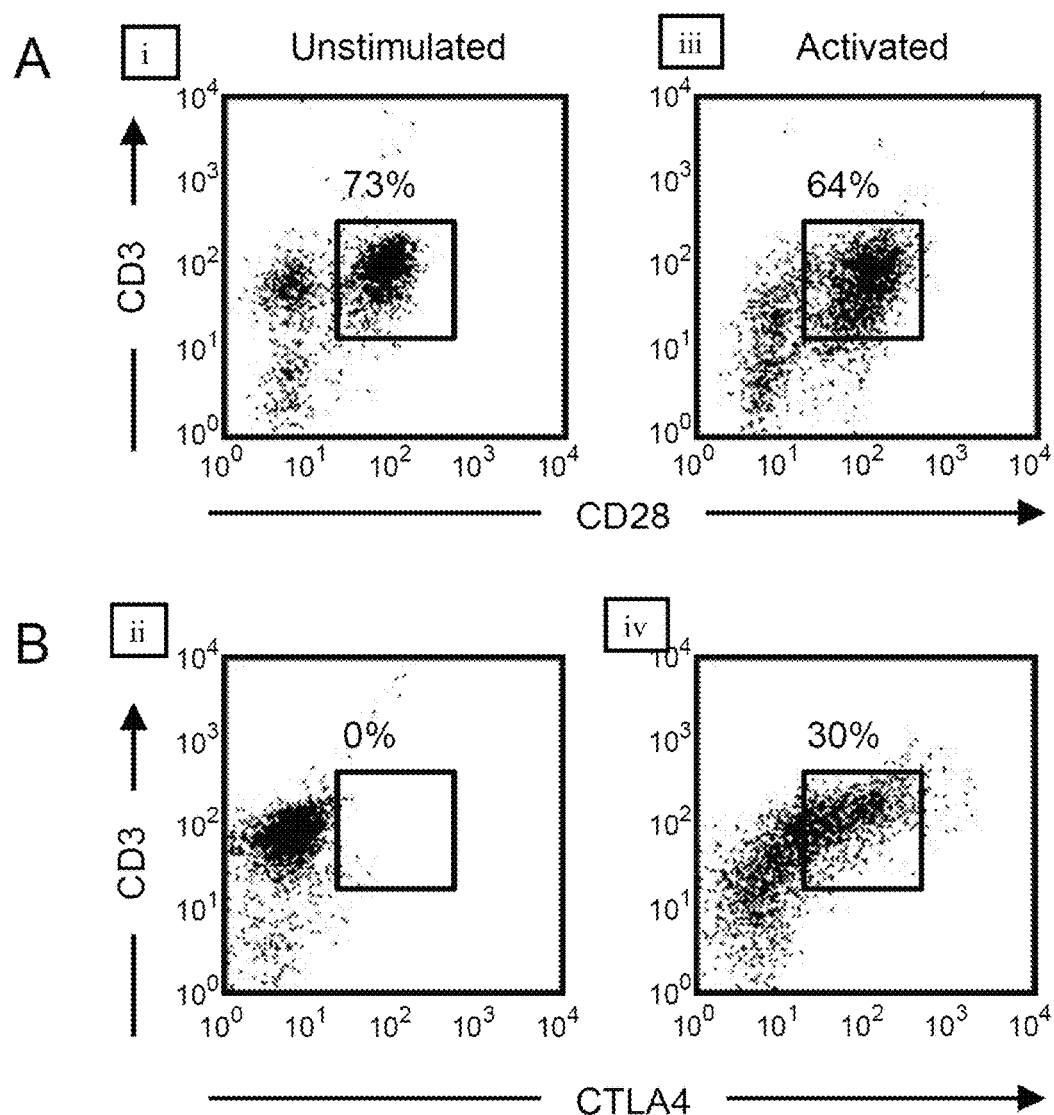
FIG. 7 shows that PHA-activated human PBMC express CTLA4 (iv) and CD28 (iii). Unstimulated PBMC (ii) and (i) from healthy donors were activated with PHA, stained for CD3/CTLA4 (iv), and CD3/CD28 (iii), and analyzed by flow cytometry. Data are representative of 2 independent experiments.

T cell suppression is also mediated by CD80-CTLA4 interactions (35, 36), raising the possibility that sCD80-Fc may contribute to immune suppression by binding to CTLA4 on activated T cells. As seen in FIG. 4, sCD80-Fc increases, rather than decreases, T cell production of IFN suggesting that sCD80-Fc does not interact with T cell-expressed CTLA4. However, the lack of suppression could be due to the absence of CTLA4 on PHA-activated T cells. To test this possibility, human PBMC were activated for 72 hrs with PHA and subsequently stained for CD3 and CTLA4 (FIG. 7B). 30% percent of activated CD3+ cells were CTLA4+. Therefore, PHA-activated T cells are potentially susceptible to CTLA4-mediated immune suppression; however, sCD80-Fc does not appear to induce suppression via CTLA4.

Discussion

As discussed above, it has previously been reported that co-expression of membrane-bound CD80 on PDL1+ human tumor cells prevents PDL1-PD1-mediated immune suppression and restores activation of human T cells (22). The results shown herein extend these findings to murine tumor cells, and importantly demonstrates that a soluble form of the extracellular domains of human CD80 (sCD80-Fc) similarly counteracts PDL1-PD1-mediated T cell apoptosis. Soluble CD80 appears to be more effective than antibodies to either PDL1 or PD1 in preventing PDL1-mediated immune suppression, thus suggesting that soluble CD80 is a potentially useful therapeutic agent for enhancing anti-tumor immunity in cancer patients.

In addition to binding to PDL1, CD80 also binds to CTLA4 (35, 36). Therefore, soluble CD80 has the potential to cause T cell anergy by interacting with T cell-expressed CTLA4 (37). Since PHA-activated T cells express CTLA4 but T cell activation was robust, it is unlikely that soluble CD80 suppresses via CTLA4. The absence of CTLA4-mediated suppression could be because PDL1 and CTLA4 share a common binding region on CD80 so that CD80 binding to PDL1 sterically prevents CTLA4 binding. This possibility is supported by cross-linking studies indicating that murine PDL1 and CTLA4 interact with CD80 at overlapping sites (4). However, CD80 mutants have been generated that do not bind CTLA4 but retain the ability to bind PDL1 (unpublished data), suggesting that PDL1 and CTLA4 do not share a common binding site on CD80. It is also unlikely that the lack of suppression via CTLA4 is due to preferential binding of CD80 to PDL1 vs. CTLA4 because human CD80 and CTLA4 interact more strongly ($K_D=0.4$ μM) than human CD80 and PDL1 ($K_D=-1.4$ μM) (4).

CD80 also functions as a costimulatory signal by binding to T cell-expressed CD28 and therefore could cause autoimmunity (33). Since human CD80 binds PDL1 more tightly than it binds CD28 ($K_D=-1.4$ μM vs. 4 μM, respectively) (4), it is theorized that soluble CD80 will preferentially bind to PDL1 rather than to CD28. This theory is supported by the anti-CD28 antibody experiments of FIG. 5C, which indicate that soluble CD80 has minimal costimulatory activity. Additionally, it was observed that 65% of PHA-activated PBMC express PDL1 raising the possibility that sCD80-Fc could also prevent PDL1-PD1 interactions between PDL1+ and PD1+PBMC.

In previous studies conducted by the inventors of the present invention, three anti-PDL1 mAbs failed to detect PDL1 on human tumor cells expressing membrane bound CD80 (22). Two of these antibodies (29E.2A3 and MIH1) were previously reported to recognize epitopes in the PDL1-CD80 binding region (21), while the binding site of the third antibody (27A2) was unknown. It was observed herein that pretreatment with 5H1 allows binding of anti-PDL1 mAb 29E.2A3, but not anti-PDL1 mAbs MIH1 or 27A2. These observations confirm that mAb 29E.2A3 reacts with an epitope on PDL1 within the PDL1-CD80 binding region, and that the 5H1 mAb disrupts PDL1-CD80 interactions to reveal this previously hidden epitope. The absence of binding of mAbs MIH1 and 27A2, following treatment with mAb 5H1, suggests that mAb 5H1 only partially dissociates CD80-PDL1 interactions and that the epitopes detected by mAb MIH1 and 27A2 remain blocked by CD80.

It is surprising that soluble CD80 is more effective than mAbs to PDL1 or PD1 in preventing PDL1-PD1-mediated suppression. Given that the binding constants of antibodies for PDL1 or PD1 are typically several orders of magnitude stronger than that of soluble CD80 to PDL1, one would expect antibodies to be more effective in blocking PDL1-PD1 interactions. Structural studies (4, 21) and results shown herein are consistent with the concept that soluble CD80 prevents PDL1-PD1 interactions by steric blocking, and antibodies to PDL1 and PD1 are thought to act in a similar fashion. Whether the differential effects of soluble CD80 vs. antibodies are due to additional mechanisms is unknown. However, if soluble CD80 and antibodies maintain T cell activation via independent or partially overlapping mechanisms, then these two reagents would be more efficacious than either reagent alone due to either an additive or synergistic effect.

REFERENCES

The contents of all references cited herein are incorporated by reference herein for all purposes.

1. Dong, H., S. E. Strome, D. R. Salomao, H. Tamura, F. Hirano, D. B. Flies, P. C. Roche, J. Lu, G. Zhu, K. Tamada, V. A. Lennon, E. Celis, and L. Chen. 2002. Tumor-associated B7-H1 promotes T-cell apoptosis: a potential mechanism of immune evasion. *Nat Med* 8:793-800.

2. Latchman, Y. E., S. C. Liang, Y. Wu, T. Chernova, R. A. Sobel, M. Klemm, V. K. Kuchroo, G. J. Freeman, and A. H. Sharpe. 2004. PD-L1-deficient mice show that PD-L1 on T cells, antigen-presenting cells, and host tissues negatively regulates T cells. *Proc Natl Acad Sci USA* 101:10691-10696.

3. Azuma, T., S. Yao, G. Zhu, A. S. Flies, S. J. Flies, and L. Chen. 2008. B7-H1 is a ubiquitous antiapoptotic receptor on cancer cells. *Blood* 111:3635-3643.

4. Butte, M. J., M. E. Keir, T. B. Phamduy, A. H. Sharpe, and G. J. Freeman. 2007. Programmed death-1 ligand 1 interacts specifically with the B7-1 costimulatory molecule to inhibit T cell responses. Immunity 27:111-122.

5. Park, J. J., R. Omiya, Y. Matsumura, Y. Sakoda, A. Kuramasu, M. M. Augustine, S. Yao, F. Tsushima, H. Narazaki, S. Anand, Y. Liu, S. E. Strome, L. Chen, and K. Tamada. 2010. B7-H1/CD80 interaction is required for the induction and maintenance of peripheral T-cell tolerance. Blood 116:1291-1298.

6. Francisco, L. M., V. H. Salinas, K. E. Brown, V. K. Vanguri, G. J. Freeman, V. K. Kuchroo, and A. H. Sharpe. 2009. PD-L1 regulates the development, maintenance, and function of induced regulatory T cells. *The Journal of Experimental Medicine* 206:3015-3029.

7. Brown, J. A., D. M. Dorfman, F. R. Ma, E. L. Sullivan, O. Munoz, C. R. Wood, E. Greenfield, and G. J. Freeman. 2003. Blockade of programmed death-1 ligands on dendritic cells enhances T cell activation and cytokine production. *J Immunol* 170:1257-1266.

8. Chen, L. 2004. Co-inhibitory molecules of the B7-CD28 family in the control off T-cell immunity. *Nat Rev Immunol* 4:336-347.

9. Parsa, A. T., J. S. Waldron, A. Panner, C. A. Crane, I. F. Parney, J. J. Barry, K. E. Cachola, J. C. Murray, T. Tihan, M. C. Jensen, P. S. Mischel, D. Stokoe, and R. O. Pieper. 2007. Loss of tumor suppressor PTEN function increases B7-H1 expression and immunoresistance in glioma. *Nature Medicine* 13:84-88.

10. Thompson, R. H., S. M. Kuntz, B. C. Leibovich, H. Dong, C. M. Lohse, W. S. Webster, S. Sengupta, I. Frank, A. S. Parker, H. Zincke, M. L. Blute, T. J. Sebo, J. C. Cheville, and E. D. Kwon. 2006. Tumor B7-H1 is associated with poor prognosis in renal cell carcinoma patients with long-term follow-up. *Cancer Res* 66:3381-3385.

11. Mu, C. Y., J. A. Huang, Y. Chen, C. Chen, and X. G. Zhang. 2011. Highexpression of PD-L1 in lung cancer may contribute to poor prognosis and tumor cells immune escape through suppressing tumor infiltrating dendritic cells maturation. *Medical Oncology* 28:682-688.

12. Hirano, F., K. Kaneko, H. Tamura, H. Dong, S. Wang, M. Ichikawa, C. Rietz, D. B. Flies, J. S. Lau, G. Zhu, K. Tamada, and L. Chen. 2005. Blockade of B7-H1 and PD-1 by monoclonal antibodies potentiates cancer therapeutic immunity. *Cancer Res* 65:1089-1096.

13. Strome, S. E., H. Dong, H. Tamura, S. G. Voss, D. B. Flies, K. Tamada, D. Salomao, J. Cheville, F. Hirano, W. Lin, J. L. Kasperbauer, K. V. Ballman, and L. Chen. 2003. B7-H1 blockade augments adoptive T-cell immunotherapy for squamous cell carcinoma. *Cancer Res* 63:6501-6505.

14. Sakthivel, P., M. Gereke, and D. Bruder. 2011. Therapeutic intervention in cancer and chronic viral infections: Antibody mediated manipulation of PD-1/PD-L1 interaction. Rev Recent Clin Trials.

15. Curiel, T. J., S. Wei, H. Dong, X. Alvarez, P. Cheng, P. Mottram, R. Krzysiek, K. L. Knutson, B. Daniel, M. C. Zimmermann, O. David, M. Burow, A. Gordon, N. Dhurandhar, L. Myers, R. Berggren, A. Hemminki, R. D. Alvarez, D. Emilie, D. T. Curiel, L. Chen, and W. Zou. 2003. Blockade of B7-H1 improves myeloid dendritic cell-mediated antitumor immunity. *Nature Medicine* 9:562-567.

16. Brahmer, J. R., C. G. Drake, I. Wollner, J. D. Powderly, J. Picus, W. H. Sharfman, E. Stankevich, A. Pons, T. M. Salay, T. L. McMiller, M. M. Gilson, C. Wang, M. Selby, J. M. Taube, R. Anders, L. Chen, A. J. Korman, D. M. Pardoll, I. Lowy, and S. L. Topalian. 2010. Phase I study of single-agent anti-programmed death-1 (MDX-1106) in refractory solid tumors: safety, clinical activity, pharmacodynamics, and immunologic correlates. *J Clin Oncol* 28:3167-3175.

17. Brahmer, J. R., S. S. Tykodi, L. Q. Chow, W. J. Hwu, S. L. Topalian, P. Hwu, C. G. Drake, L. H. Camacho, J. Kauh, K. Odunsi, H. C. Pitot, O. Hamid, S. Bhatia, R. Martins, K. Eaton, S. Chen, T. M. Salay, S. Alaparthy, J. F. Grosso, A. J. Korman, S. M. Parker, S. Agrawal, S. M. Goldberg, D. M. Pardoll, A. Gupta, and J. M. Wigginton. 2012. Safety and activity of anti-PD-L1 antibody in patients with advanced cancer. *N Engl J Med* 366:2455-2465.

18. Topalian, S. L., F. S. Hodi, J. R. Brahmer, S. N. Gettinger, D. C. Smith, D. F. McDermott, J. D. Powderly, R. D. Carvajal, J. A. Sosman, M. B. Atkins, P. D. Leming, D. R. Spigel, S. J. Antonia, L. Horn, C. G. Drake, D. M. Pardoll, L. Chen, W. H. Sharfman, R. A. Anders, J. M. Taube, T. L. McMiller, H. Xu, A. J. Korman, M. Jure-Kunkel, S. Agrawal, D. McDonald, G. D. Kollia, A. Gupta, J. M. Wigginton, and M. Sznol. 2012. Safety, activity, and immune correlates of anti-PD-1 antibody in cancer. *N Engl J Med* 366:2443-2454.

19. Ascierto, P. A., E. Simeone, M. Sznol, Y. X. Fu, and I. Melero. 2010. Clinical experiences with anti-CD137 and anti-PD1 therapeutic antibodies. Semin Oncol 37:508-516.

20. Ascierto, P. A., E. Simeone, M. Sznol, Y. X. Fu, and I. Melero. 2011. Clinical experiences with anti-CD137 and anti-PD1 therapeutic antibodies. *Semin Oncol* 37:508-516.

21. Butte, M. J., V. Pena-Cruz, M. J. Kim, G. J. Freeman, and A. H. Sharpe. 2008. Interaction of human PD-L1 and B7-1. *Mol Immunol* 45:3567-3572.

22. Haile, S. T., J. J. Bosch, N. I. Agu, A. M. Zeender, P. Somasundaram, M. K. Srivastava, S. Britting, J. B. Wolf, B. R. Ksander, and S. Ostrand-Rosenberg. 2011. Tumor cell programmed death ligand 1-mediated T cell suppression is overcome by coexpression of CD80. J Immunol 186:6822-6829.

23. Srivastava, M. K., J. J. Bosch, A. L. Wilson, M. J. Edelman, and S. OstrandRosenberg. 2010. WIC II lung cancer vaccines prime and boost tumor-specific CD4+ Tcells that cross-react with multiple histologic subtypes of nonsmall cell lung cancer cells. *Int J Cancer* 127:2612-2621.

24. Pulaski, B. A., and S. Ostrand-Rosenberg. 1998. Reduction of established spontaneous mammary carcinoma metastases following immunotherapy with major histocompatibility complex class II and B7.1 cell-based tumor vaccines. *Cancer Res* 58:1486-1493.

25. Srivastava, M. K., J. J. Bosch, J. A. Thompson, B. R. Ksander, M. J. Edelman, and S. Ostrand-Rosenberg. 2008. Lung cancer patients' CD4(+) T cells are activated in vitro by MHC II cell-based vaccines despite the presence of myeloid-derived suppressor cells. *Cancer Immunol Immunother* 57:1493-1504.

26. Dissanayake, S. K., J. A. Thompson, J. J. Bosch, V. K. Clements, P. W. Chen, B. R. Ksander, and S. Ostrand-Rosenberg. 2004. Activation of tumor-specific CD4(+) T lymphocytes by major histocompatibility complex class II tumor cell vaccines: a novel cell-based immunotherapy. *Cancer Res* 64:1867-1874.

27. Thompson, J. A., M. K. Srivastava, J. J. Bosch, V. K. Clements, B. R. Ksander, and S. Ostrand-Rosenberg. 2008. The absence of invariant chain in MHC II cancer vaccines enhances the activation of tumor-reactive type 1 CD4+ T lymphocytes. *Cancer Immunol Immunother* 57:389-398.

28. Bosch, J. J., J. A. Thompson, M. K. Srivastava, U. K. Iheagwara, T. G. Murray, M. Lotem, B. R. Ksander, and S. Ostrand-Rosenberg. 2007. MHC class II-transduced tumor cells originating in the immune-privileged eye prime and boost CD4(+) T lymphocytes that cross-react with primary and metastatic uveal melanoma cells. Cancer Res 67:4499-4506.

29. Blank, C., I. Brown, A. C. Peterson, M. Spiotto, Y. Iwai, T. Honjo, and T. F. Gajewski. 2004. PD-L1/B7H-1 inhibits the effector phase of tumor rejection by T cell receptor (TCR) transgenic CD8+ T cells. *Cancer Res* 64:1140-1145.

30. Schmidt, S. R. 2009. Fusion-proteins as biopharmaceuticals—applications and challenges. Curr Opin Drug Discov Devel 12:284-295.

31. Zhang, L., T. F. Gajewski, and J. Kline. 2009. PD-1/PD-L1 interactions inhibit antitumor immune responses in a murine acute myeloid leukemia model. *Blood* 114:1545-1552.

32. Peng, W., C. Liu, C. Xu, Y. Lou, J. Chen, Y. Yang, H. Yagita, W. W. Overwijk, G. Lizee, L. Radvanyi, and P. Hwu. 2012. PD-1 BLOCKADE ENHANCES T CELL MIGRATION TO TUMORS BY ELEVATING IFN-gamma INDUCIBLE CHEMOKINES. *Cancer Res*. (soon to be published).

33. Jenkins, M., P. Taylor, S. Norton, and K. Urdahl. 1991. CD28 delivers a costimulatory signal involved in antigen-specific IL-2 production by human T cells. *J Immunol* 147:2461-2467.

34. Norton, S., L. Zuckerman, K. Urdahl, R. Shefner, J. Miller, and M. Jenkins. 1992. The CD28 ligand, B7, enhances IL-2 production by providing a costimulatory signal to T cells. *J Immunol* 149:1556-1617.

35. Peach, R. J., J. Bajorath, J. Naemura, G. Leytze, J. Greene, A. Aruffo, and P. S. Linsley. 1995. Both extracellular immunoglobin-like domains of CD80 contain residues critical for binding T cell surface receptors CTLA-4 and CD28. *The Journal of biological chemistry* 270:21181-21187.

36. Stamper, C. C., Y. Zhang, J. F. Tobin, D. V. Erbe, S. Ikemizu, S. J. Davis, M. L. Stahl, J. Seehra, W. S. Somers, and L. Mosyak. 2001. Crystal structure of the B7-1/CTLA-4 complex that inhibits human immune responses. *Nature* 410:608-611.

37. Salomon, B., and J. A. Bluestone. 2001. Complexities of CD28/B7: CTLA-4 costimulatory pathways in autoimmunity and transplantation. *Annual review of immunology* 19:225-252.

The invention claimed is:

1. A mutated CD80 peptide consisting of the amino acid sequence of SEQ ID NO: 15.

2. A chimeric peptide comprising a mutated CD80 amino acid sequence and a Fc IgG1 amino acid sequence, wherein the mutated CD80 amino acid sequence consists of the amino acid sequence of SEQ ID NO: 15.

3. The chimeric peptide of claim 2, wherein the Fc_IgG1 amino acid sequence comprises SEQ ID NO: 8 or SEQ ID NO: 12.

4. A chimeric polypeptide comprising (i) the mutated CD80 peptide of claim 1 and (ii) a transmembrane sequence SEQ ID NO: 11 and/or a signaling sequence SEQ ID NO: 10.

* * * * *